(12) United States Patent
Karp et al.

(10) Patent No.: US 7,028,536 B2
(45) Date of Patent: Apr. 18, 2006

(54) SEALING INTERFACE FOR MICROFLUIDIC DEVICE

(75) Inventors: Christoph D. Karp, Pasadena, CA (US); Marci Pezzuto, Altadena, CA (US); Steven E. Hobbs, West Hills, CA (US)

(73) Assignee: Nanostream, Inc., Pasadena, CA (US)

( * ) Notice: Subject to any disclaimer, the term of this patent is extended or adjusted under 35 U.S.C. 154(b) by 78 days.

(21) Appl. No.: 10/880,656

(22) Filed: Jun. 29, 2004

(65) Prior Publication Data

US 2005/0284213 A1  Dec. 29, 2005

(51) Int. Cl.
*G01N 30/00* (2006.01)

(52) U.S. Cl. .................................................. 73/61.52
(58) Field of Classification Search ............... 73/61.52, 73/61.55, 61.56; 210/656; 422/70; 436/161, 436/162
See application file for complete search history.

(56) References Cited

U.S. PATENT DOCUMENTS

| | | | |
|---|---|---|---|
| 3,449,938 A | 6/1969 | Giddings | 73/23 |
| 3,680,576 A | 8/1972 | Kiwak | 137/81.5 |
| 4,301,139 A | 11/1981 | Feingers et al. | 424/1 |
| 4,424,127 A | 1/1984 | Roeraade | 210/198.2 |
| 4,496,461 A | 1/1985 | Leeke et al. | 210/198.2 |
| 4,604,198 A | 8/1986 | Dailey et al. | 210/198.2 |
| 4,671,871 A | 6/1987 | Székely et al. | 210/198.3 |
| 4,891,120 A | 1/1990 | Sethi et al. | 204/299 R |
| 4,946,795 A | 8/1990 | Gibbons et al. | 436/179 |
| 5,135,627 A | 8/1992 | Soane | 204/182.8 |
| 5,190,658 A | 3/1993 | Vilenchik et al. | 210/656 |
| 5,194,133 A | 3/1993 | Clark et al. | 204/299 R |
| 5,376,252 A | 12/1994 | Ekström et al. | 204/299 R |
| 5,443,890 A | 8/1995 | Öhman | 428/167 |
| 5,453,163 A | 9/1995 | Yan | 204/180.1 |
| 5,478,751 A | 12/1995 | Oosta et al. | 436/165 |
| 5,658,413 A | 8/1997 | Kaltenbach et al. | 156/272.8 |
| 5,667,676 A | 9/1997 | Alaska | 210/198.2 |
| 5,698,299 A | 12/1997 | Schmidt et al. | 428/209 |
| 5,744,366 A | 4/1998 | Kricka et al. | 436/63 |
| 5,757,482 A | 5/1998 | Fuchs et al. | 356/246 |

(Continued)

FOREIGN PATENT DOCUMENTS

EP   1 106 244 A2   6/2001

(Continued)

OTHER PUBLICATIONS

Ericson, Christer et., *Electroosmosis- and Pressure-Driven Chromatography in Chips Using Continuous Bed,* "Analytical Chemistry," vol. 72, No. 1, Jan. 1, 2000.

(Continued)

*Primary Examiner*—Charles Garber
(74) *Attorney, Agent, or Firm*—Vincent K. Gustafson; Intellectual Property/Technology Law

(57) ABSTRACT

A threadless interface for a fluidic system includes a microfluidic device having an outer surface and an internal near-surface channel having a first width and disposed at a first depth relative to the outer surface, with the first width being less than about two times the first depth. A fluidic seal engages the outer surface and exerts an elevated contact pressure against at least a portion of the outer surface without substantially occluding the channel. A preferred seal includes a raised boss. A fault tolerant flow path design can accommodate misalignment between adjacent device layers without detrimentally affecting fluid flow capability. The interface may be used in a microfluidic system for performing parallel analyses such as high performance liquid chromatography.

36 Claims, 11 Drawing Sheets

U.S. PATENT DOCUMENTS

| | | | | |
|---|---|---|---|---|
| 5,792,943 | A | 8/1998 | Craig | 73/61.52 |
| 5,804,701 | A | 9/1998 | Berger | 73/23.42 |
| 5,872,010 | A | 2/1999 | Karger et al. | 436/173 |
| 5,890,745 | A | 4/1999 | Kovacs | 285/24 |
| 6,033,544 | A | 3/2000 | Demers et al. | 204/450 |
| 6,074,725 | A | 6/2000 | Kennedy | 428/188 |
| 6,080,318 | A | 6/2000 | Gumm et al. | 210/659 |
| 6,086,740 | A | 7/2000 | Kennedy | 204/601 |
| 6,090,278 | A | 7/2000 | Lally et al. | 210/198.2 |
| 6,103,199 | A | 8/2000 | Bjornson et al. | 422/100 |
| 6,149,815 | A | 11/2000 | Sauter | 210/635 |
| 6,197,198 | B1 | 3/2001 | Messinger et al. | 210/656 |
| 6,210,986 | B1 | 4/2001 | Arnold et al. | 438/42 |
| 6,221,252 | B1 | 4/2001 | Hargro et al. | 210/656 |
| 6,240,790 | B1 | 6/2001 | Swedberg et al. | 73/863.21 |
| 6,258,263 | B1 | 7/2001 | Henderson et al. | 210/198.2 |
| 6,264,892 | B1 | 7/2001 | Kaltenbach et al. | 422/68.1 |
| 6,273,478 | B1 | 8/2001 | Benett et al. | 285/346 |
| 6,293,012 | B1 | 9/2001 | Moles | 29/890.124 |
| 6,296,771 | B1 | 10/2001 | Miroslav | 210/656 |
| 6,387,234 | B1 | 5/2002 | Yeung et al. | 204/451 |
| 6,409,072 | B1 | 6/2002 | Breuer et al. | 228/111.5 |
| 6,418,968 | B1 | 7/2002 | Pezzuto et al. | 137/833 |
| 6,432,290 | B1 | 8/2002 | Harrison et al. | 204/453 |
| 6,444,150 | B1 | 9/2002 | Arnold | 264/69 |
| 6,444,461 | B1 | 9/2002 | Knapp et al. | 435/283.1 |
| 6,461,515 | B1 | 10/2002 | Safir et al. | 210/656 |
| 6,485,690 | B1 | 11/2002 | Pfost et al. | 422/102 |
| 6,491,816 | B1 | 12/2002 | Petro | 210/198.2 |
| 6,494,614 | B1 | 12/2002 | Bennett et al. | 366/336 |
| 6,497,138 | B1 | 12/2002 | Abdel-Rahman et al. | 73/23.42 |
| 6,508,938 | B1 | 1/2003 | Maiefski et al. | 210/659 |
| 6,527,890 | B1 | 3/2003 | Briscoe et al. | 156/89.11 |
| 6,533,840 | B1 | 3/2003 | Martin et al. | 95/45 |
| 6,537,506 | B1 | 3/2003 | Schwalbe et al. | 422/130 |
| 6,557,427 | B1 | 5/2003 | Weigl et al. | 73/863.31 |
| 6,572,830 | B1 | 6/2003 | Burdon et al. | 422/186.29 |
| 6,581,441 | B1 | 6/2003 | Paul | 73/61.52 |
| 6,612,153 | B1 | 9/2003 | White et al. | 73/23.42 |
| 6,613,224 | B1 | 9/2003 | Strand | 210/198.2 |
| 6,623,860 | B1 | 9/2003 | Hu et al. | 428/411.1 |
| 6,627,433 | B1 | 9/2003 | Frazier et al. | 435/288.7 |
| 6,635,226 | B1 | 10/2003 | Tso et al. | 422/129 |
| 6,641,783 | B1 | 11/2003 | Pidgeon et al. | 422/70 |
| 6,645,377 | B1 | 11/2003 | Egorov et al. | 210/198.2 |
| 6,656,431 | B1 | 12/2003 | Holl et al. | 422/68.1 |
| 6,660,149 | B1 | 12/2003 | Karger et al. | 204/601 |
| 6,663,697 | B1 | 12/2003 | Kottenstette et al. | 96/101 |
| 6,664,104 | B1 | 12/2003 | Pourahmadi et al. | 435/288.6 |
| 6,743,356 | B1 | 6/2004 | Fermier et al. | 210/198.2 |
| 6,749,749 | B1 | 6/2004 | Xie et al. | 210/198.2 |
| 6,749,814 | B1 | 6/2004 | Bergh et al. | 422/130 |
| 6,812,030 | B1 | 11/2004 | Ozbal et al. | 436/50 |
| 6,814,859 | B1 | 11/2004 | Koehler et al. | 210/198.2 |
| 2001/0013494 | A1 | 8/2001 | Maiefski et al. | 210/656 |
| 2002/0001815 | A1 | 1/2002 | Hindsgaul et al. | 435/7.1 |
| 2002/0003001 | A1 | 1/2002 | Weigl et al. | 137/806 |
| 2002/0017484 | A1 | 2/2002 | Dourdeville | 210/198.2 |
| 2002/0048536 | A1 | 4/2002 | Bergh et al. | 422/130 |
| 2002/0112961 | A1 | 8/2002 | O'Connor et al. | 204/601 |
| 2002/0158022 | A1 | 10/2002 | Huang et al. | 210/656 |
| 2002/0189947 | A1 | 12/2002 | Paul et al. | 204/461 |
| 2002/0199094 | A1 | 12/2002 | Strand et al. | 713/150 |
| 2003/0019816 | A1 | 1/2003 | Mincsovics et al. | 210/741 |
| 2003/0094415 | A1 | 5/2003 | Tanimura | 210/656 |
| 2003/0150806 | A1 | 8/2003 | Hobbs et al. | 210/635 |
| 2003/0200794 | A1* | 10/2003 | Paul | 73/54.05 |
| 2003/0230524 | A1 | 12/2003 | Soga et al. | 210/198.2 |
| 2004/0020834 | A1 | 2/2004 | Mincsovics et al. | 210/198.2 |
| 2004/0072337 | A1 | 4/2004 | Moon et al. | 435/287.2 |
| 2004/0089607 | A1 | 5/2004 | Hobbs et al. | 210/656 |
| 2004/0104173 | A1 | 6/2004 | Manach et al. | 210/656 |
| 2004/0134845 | A1 | 7/2004 | Paul et al. | 210/198.2 |
| 2004/0219071 | A1 | 11/2004 | Ozbal et al. | 422/100 |
| 2005/0048669 | A1 | 3/2005 | Hobbs et al. | 436/180 |

FOREIGN PATENT DOCUMENTS

| | | |
|---|---|---|
| EP | 1 178 309 A1 | 2/2002 |
| WO | WO 92/03726 | 3/1992 |
| WO | WO 95/02178 | 1/1995 |
| WO | WO 97/30347 | 8/1997 |
| WO | WO 98/04909 | 2/1998 |
| WO | WO 99/19717 | 4/1999 |
| WO | WO 99/34909 | 7/1999 |
| WO | WO 00/31528 | 6/2000 |
| WO | WO 00/72970 A1 | 12/2000 |
| WO | WO 01/09598 A1 | 2/2001 |
| WO | WO 01/025138 A1 | 4/2001 |
| WO | WO 01/30490 A1 | 5/2001 |
| WO | WO 02/22250 A2 | 3/2002 |
| WO | WO 02/28509 A2 | 4/2002 |
| WO | WO 02/28532 A2 | 4/2002 |
| WO | WO 03/002226 A1 | 1/2003 |
| WO | WO 03/054524 A1 | 7/2003 |

OTHER PUBLICATIONS

Poole, Colin F., "4.5 Column Preparation," *The essence of chromatography*, 2003 Elsevier Science B.V., Amsterdam, The Netherlands, pp. 393-401.

Poole, Colin F., "5.6 Coupled-Column Systems," *The essence of chromatography*, 2003 Elsevier Science B.V., Amsterdam, The Netherlands, pp. 451-455.

Poole, Colin F., "8.4.2 Column Technology," *The essence of chromatography*, 2003 Elsevier B.V., Amsterdam, The Netherlands, pp. 664-668.

Krull, Ira S. et al., "2.3 Techniques for Packing Capillaries," *Capillary Electrochromatography and Pressurized Flow Capillary Electrochromatography*, 2000 HNB Publishing, New York, NY, pp. 40-46.

Ocvirk, Gregor et al., *High Performance Liquid Chromatography Partially Integrated onto a Silicon Chip*, "Analytical Methods and Instrumentation," vol. 2, No. 2, 1995, pp. 74-82.

Poole, Colin F. et al., *Chromatography today*, 1991 Elsevier Science B.V., Amsterdam, The Netherlands.

Keller, H.P. et al., *Dynamic Slurry-Packing Technique for Liquid Chromatography Columns*, "Analytical Chemistry," vol. 49, No. 13, Nov. 1977.

Manz, Andreas et al., *Miniaturization fo Separation Techniques Using Planar Chip Technology*, "Journal of High Resolution Chromatography," vol. 16, Jul. 1993.

Jemere, Abebaw B. et al., "Microchip-Based Selective Preconcentration Using Protein A Immunoaffinity Chromatography," *Micro Total Analysis Systems*, 2001 Kluwer Academic Publishers, J.M. Ramsey and A. van den Berg (eds.), The Netherlands.

Manz, A. et al., *Design of an Open-tubular Column Liquid Chromatograph Using Silicon Chip Technology*, "Sensors and Actuators," B1, 1990, pp. 249-255.

González, C. et al., *Fludic interconnects for modular assembly of chemical Microsystems*, "Sensors and Actuators," B49, 1998, pp. 40-45.

Bryson, Nathan et al., "An Introduction to OPLC Operation and Applications," The Application Notebook, Jun. 2004, Bionisis SA, Le Plessis Robinson, France.

Yao, Tze-Jung et al., "Micromachined Rubber O-ring Micro-Fluidic Couplers," MEMS, 2000, Miyazaki, Japan, Jan. 23-27.

Gray, Bonnie L. et al., "Interlocking Mechanical and Microfluidic Interconnections Fabricated by Deep Reactive Ion Etching," *Micro Total Analysis Systems*, 2001 Kluwer Academic Publishers, J.M. Ramsey and A. van den Berg (eds.), The Netherlands, pp. 153-154.

Urbanek, Wolfram et al., "An investigation of the temperature dependence of Poiseuille numbers in microchannel flow," 1993 IOP Publishing Ltd.

Harris, Cheryl M., *Shrinking the LC Landscape*, "Analytical Chemistry," Feb. 1, 2003.

Bionisis S.A., Data Sheet DS101-01-B, "multiOPLC 4000 & 8000".

Holl, Mark, Ph.D. et al., "Microfluidic Materials: Polymeric Laminate Technology," Micronics, Inc., Sep. 7, 2001.

Moore, Roger E. et al., *A Microscale Electrospray Interface Incorporating a Monolithic, Poly(styrene-divinylbenzene) Support for On-Line Liquid Chromatography/Tandem Mass Spectrometry Analysis of Peptides and Proteins*, "Analytical Chemistry," vol. 70, No. 23, Dec. 1, 1998, pp. 4879-4884.

Finot, Michael et al., "High Throughput Pharmaceutical Formulation Evaluation and Analysis Using Capillary Electrochromatography on a Microfluidic Chip," *Micro Total Analysis Systems*, 2001 Kluwer Academic Publishers, J.M. Ramsey and A. van den Berg (eds.), The Netherlands.

Seki, Minoru et al., "Chromatographic Separation of Proteins on A PDMS-Polymer Chip by Pressure Flow," *Micro Total Analysis Systems*, 2001 Kluwer Academic Publishers, J.M. Ramsey and A. van den Berg (eds.), The Netherlands, pp. 48-50.

Sato, Kiichi et al., "Integrated Immunoassay System Using Multichannel Microchip for Simultaneous Determination," *Micro Total Analysis Systems*, 2001 Kluwer Academic Publishers, J.M. Ramsey and A. van den Berg (eds.), The Netherlands, pp. 511-512.

* cited by examiner

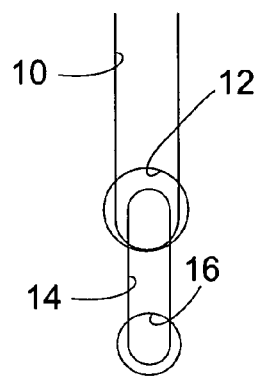
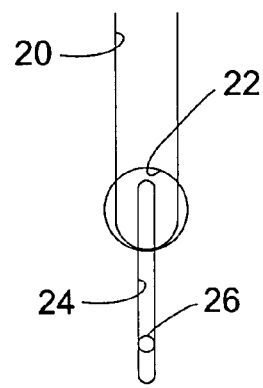
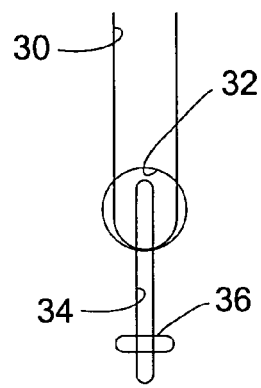
FIG._1A  FIG._2A  FIG._3A
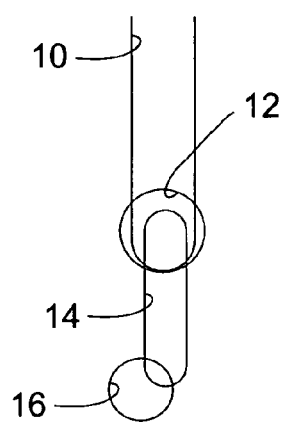
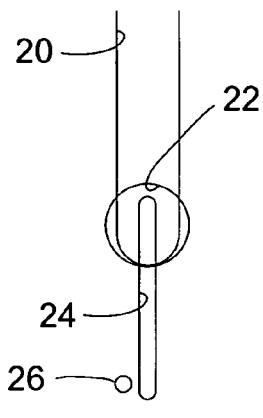
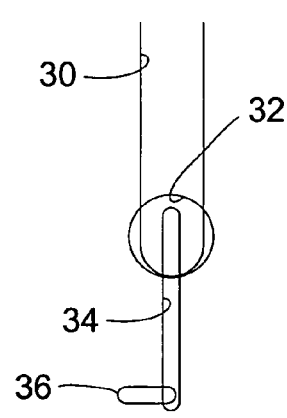
FIG._1D  FIG._2B  FIG._3D

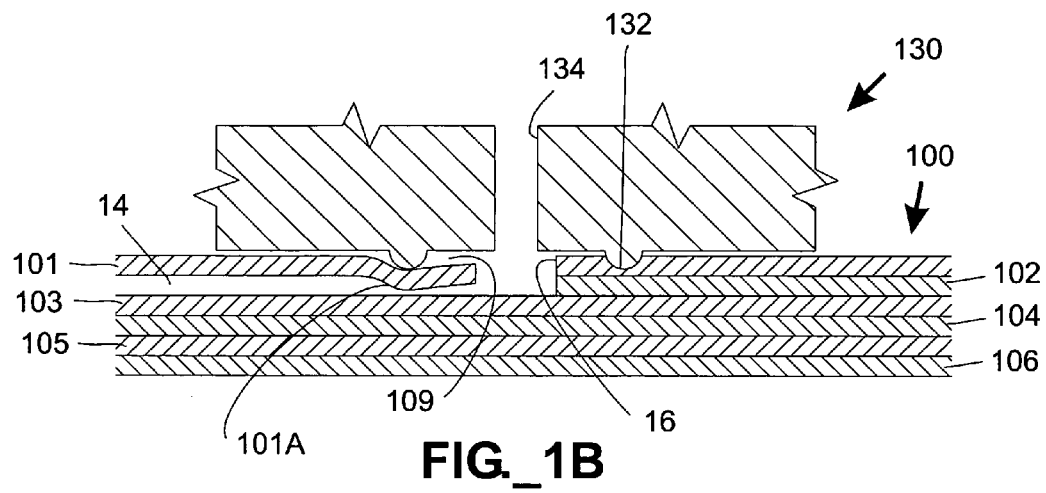
FIG._1B
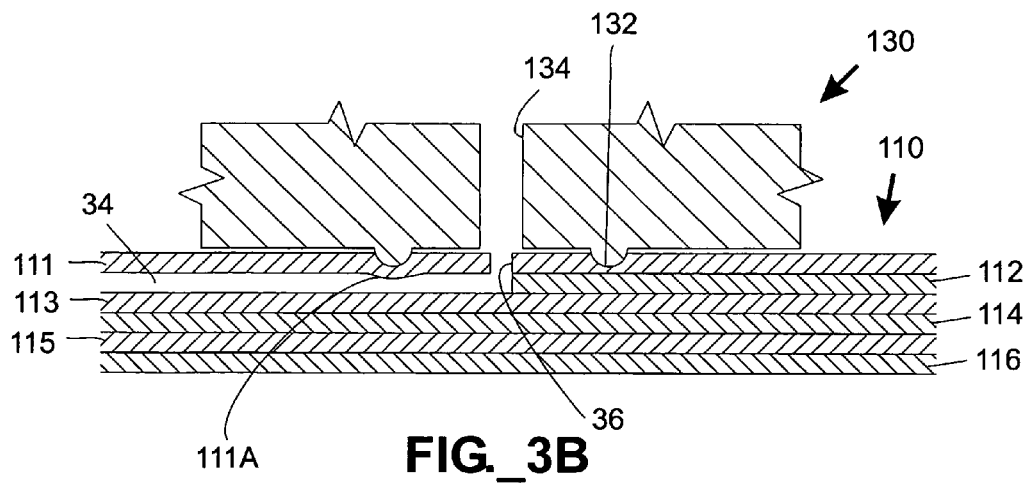
FIG._3B

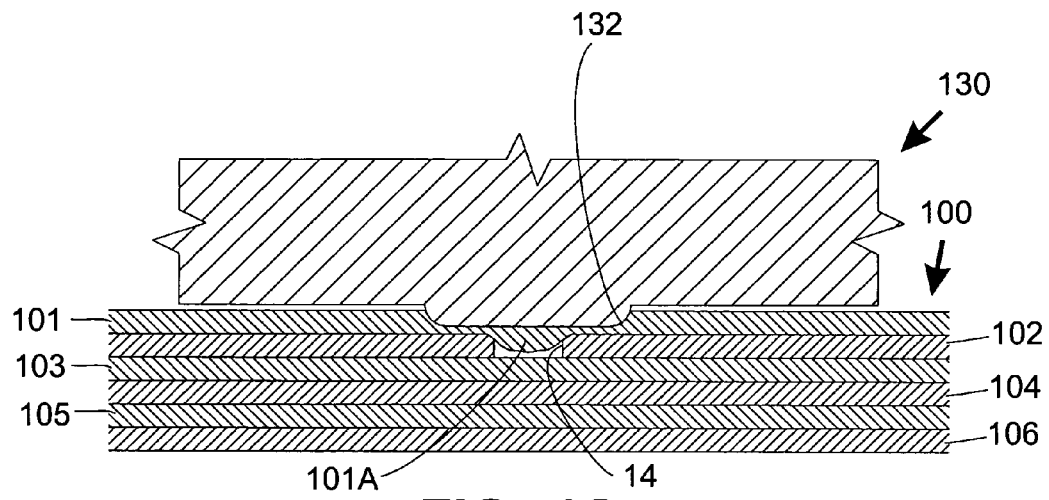
FIG._1C
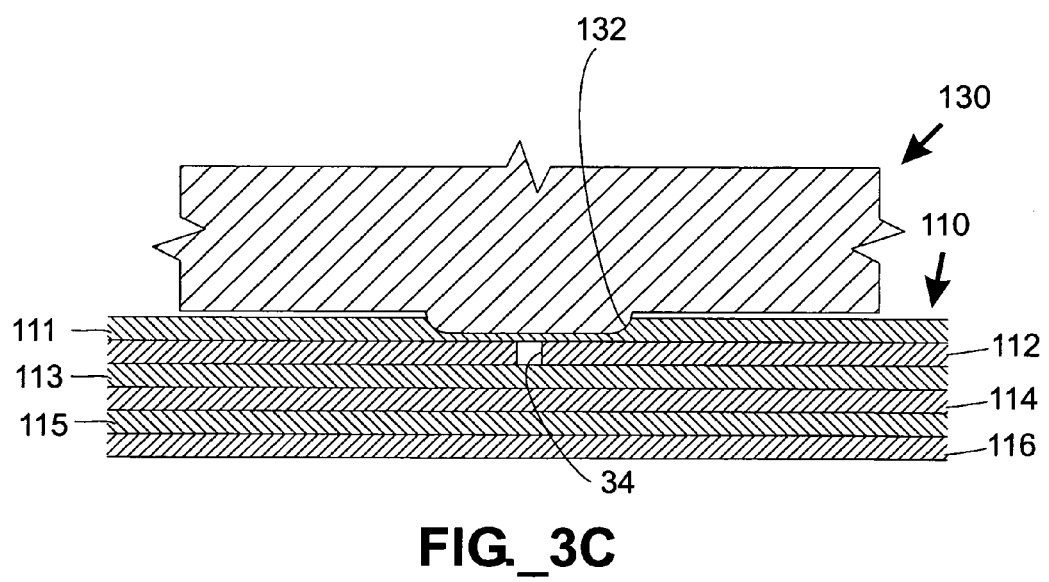
FIG._3C

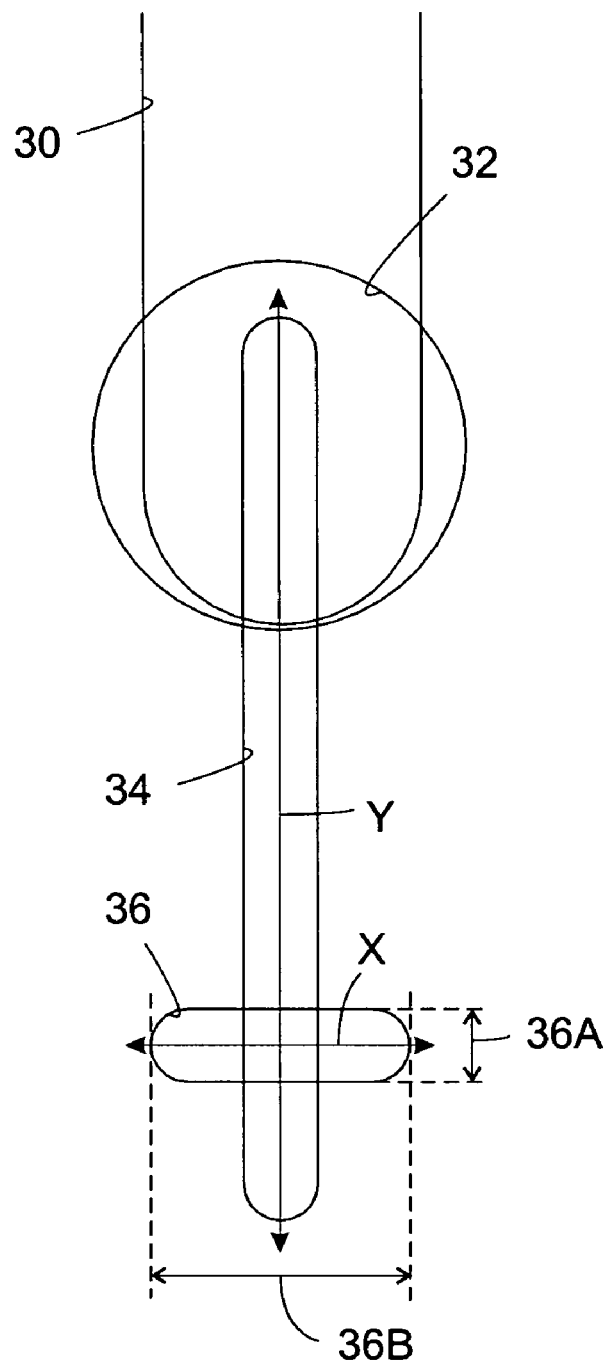
FIG._3E

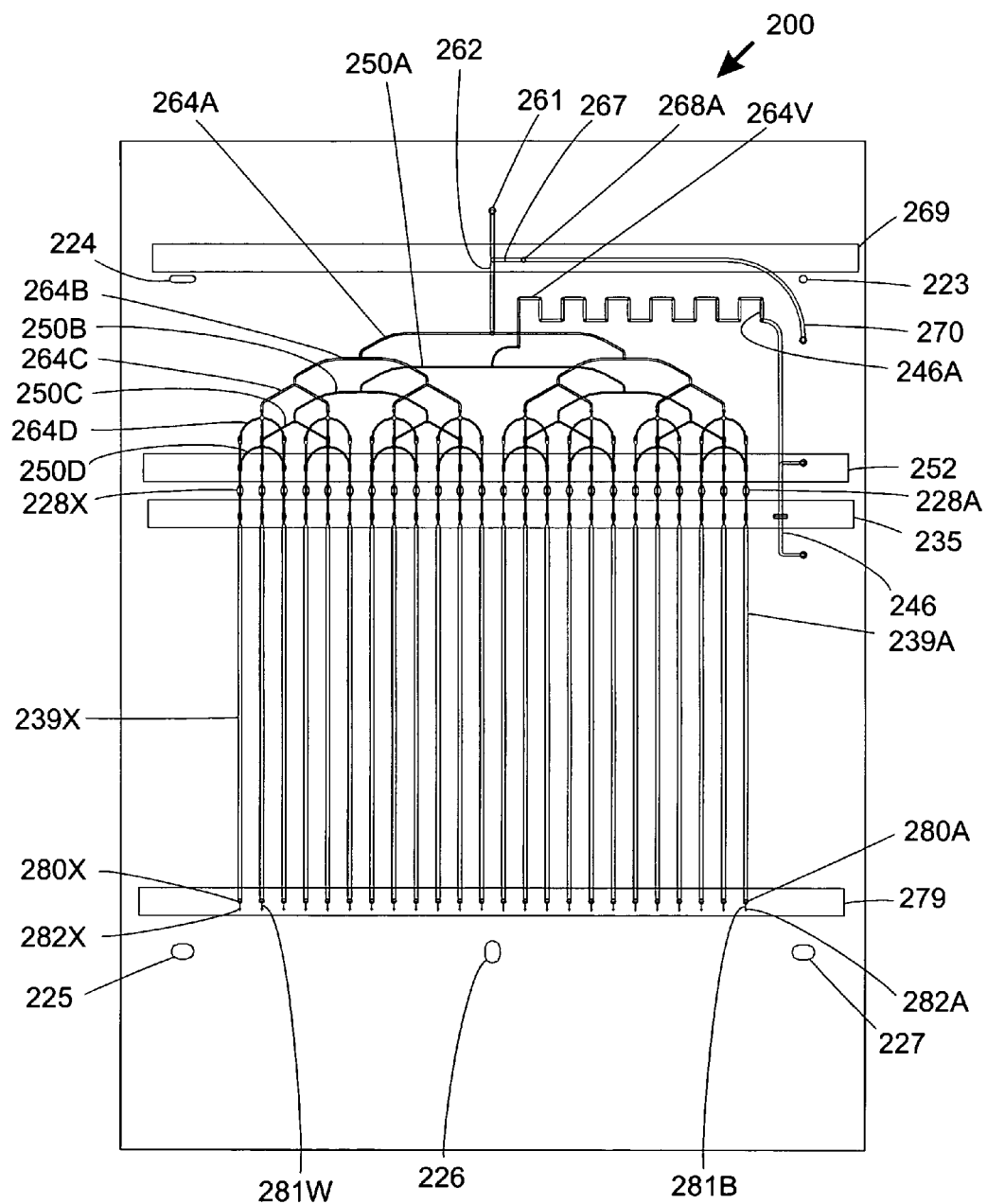
FIG._4

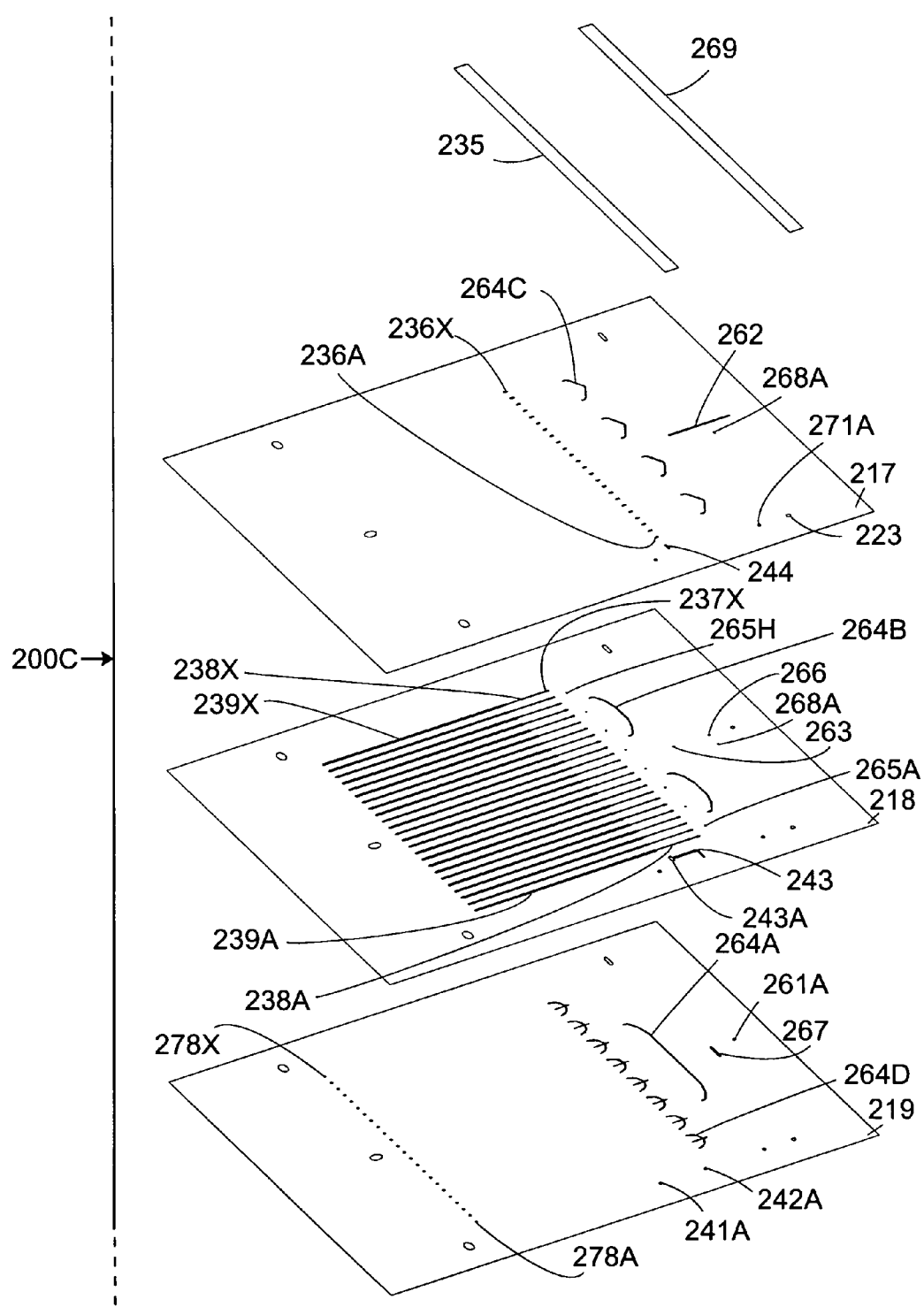
FIG._5C

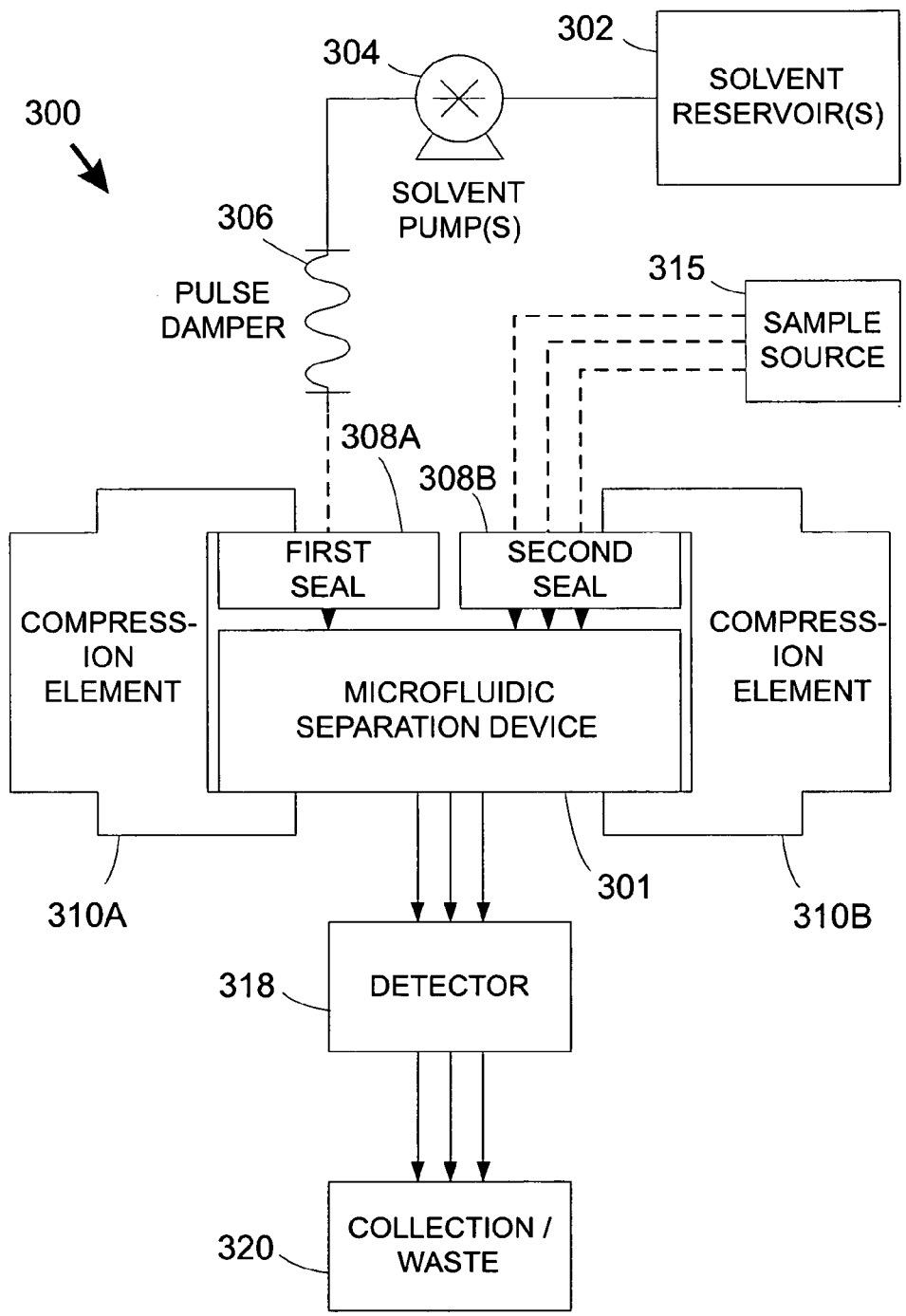
FIG._6

SEALING INTERFACE FOR MICROFLUIDIC DEVICE

FIELD OF THE INVENTION

The present invention relates to microfluidic systems, including microfluidic devices for handling and/or processing very small quantities of fluids and associated interfaces.

BACKGROUND OF THE INVENTION

There has been a growing interest in the application of microfluidic systems to a variety of technical areas, including such diverse fields as biochemical analysis, medical diagnostics, chemical synthesis, and environmental monitoring. Microfluidic systems provide certain advantages in acquiring chemical and biological information. For example, microfluidic systems permit complicated processes to be carried out using very small volumes of fluid, thus minimizing consumption of both samples and reagents. Chemical and biological reactions occur more rapidly when conducted in microfluidic volumes. Furthermore, microfluidic systems permit large numbers of complicated biochemical reactions and/or processes to be carried out in a small area (such as within a single integrated device) and facilitate the use of common control components. Examples of desirable applications for microfluidic technology include processes such as analytical chemistry; chemical and biological synthesis; DNA amplification; and screening of chemical and biological agents for activity.

Among the various branches of analytical chemistry, the field of chromatography stands to particularly benefit from microfluidic technology due to increased throughput afforded by performing multiple miniaturized-format analyses in parallel. Chromatography encompasses a number of applied methods that may be used for any of separation, identification, purification, and quantification of chemical or biochemical entities within various mixtures. In its most basic form, chromatography is a physical method of separation wherein the components to be separated are distributed between two phases, one of which is essentially stationary (the stationary phase) while the other (the mobile phase) moves in a definite direction. Separation results from differences in the distribution constants of the individual sample components between the two phases.

One subset of chromatography, liquid chromatography, utilizes a liquid mobile phase that typically includes one or more solvents. The stationary phase material typically includes packed particles having bound surface functional groups disposed within a tube commonly referred to as a "separation column." A sample is carried by the mobile phase through the stationary phase material. As the sample solution flows with the mobile phase through the stationary phase, components of the sample solution will migrate according to interactions with the stationary phase and these components are retarded to varying degrees. The time a particular component spends in the stationary phase relative to the fraction of time it spends in the mobile phase will determine its velocity through the column. Following chromatographic separation in the column, the resulting eluate stream (i.e., mobile phase and sample components) contains a series of regions having elevated concentrations of individual species, which can be detected by various techniques to identify and/or quantify the species.

Although various motive forces such as pressure-driven flow or electrokinetic (voltage-driven) flow may be used in liquid chromatography, pressure-driven flow is desirable because it permits the use of a wide range of samples and solvents. Additionally, pressure-driven flow avoids problems inherently associated with high voltage systems—such as hydrolysis, which can lead to detrimental bubble formation. Within pressure-driven systems, higher pressures generally provide greater separation efficiencies, such that pressures of several hundred pounds per square inch (psi) or more are used in conventional liquid chromatography systems. So-called "high performance liquid chromatography" or "HPLC" systems that employ high operating pressures are widely used in various industrial and academic settings.

Because of the growing demand for liquid chromatographic analysis, it would be desirable to enable multiple pressure-driven chromatographic separations to be performed simultaneously, such as in parallel. Nonetheless, the ability to perform multiple parallel separations has been limited for a variety of reasons.

One obstacle to the development of parallel high-pressure fluidic systems has been providing fluidic interconnects capable of rapid operation while reliably sealing against leakage of high-pressure fluids. Conventional tube-based chromatography systems (e.g., employing columns contained by macro-scale or capillary tubing) typically utilize low-dead-volume threaded fittings. These fittings, however, are not well-suited for use in high-throughput (i.e., parallel) separation systems because: (1) they typically require individual assembly, which limits their ability to be rapidly operated; (2) they typically require circumferential access, thus limiting their ability to be arranged in close proximity to one another; and (3) they are difficult to automate due to the need to perform steps such as aligning mating components, rotating multiple screw fittings, and so on.

To promote rapid connection to microfluidic devices, a preferred interface type would operate by threadless engagement. One example of a threadless interface is provided in WIPO International Publication Number WO 01/09598 to Holl et al., which discloses face sealing between a manifold having at least one protruding feature (e.g., a rigid tube) and a microfluidic device having an elastomeric outer layer. A bore defined in the protruding feature of the manifold is aligned with feature defined in the elastomeric outer layer of the microfluidic device such that when the protruding feature is pressed against the elastomeric outer layer, fluid can be communicated from the manifold into the microfluidic device or vice-versa. A common manifold may retain multiple tubes, and the sealing end face of each tube may have one or more ridges to provide improved sealing utility. One limitation of the Holl et al. interconnect is that it requires elastomeric materials. Elastomeric materials have limited utility in applications such as liquid chromatography, however, since they are generally incompatible with organic solvents typically used in chromatography and also may interact with samples in undesirable ways. For example, organic solvents commonly used in liquid chromatography can degrade elastomeric materials, thus causing degradation products to enter an eluate stream and potentially interfere with sample analysis. Additionally, molecules of a first sample may be adsorbed or otherwise temporarily bound to an elastomeric material during a first separation run, and such molecules may subsequently leach into an eluate stream containing a second sample during a second separation run, thus causing cross-contamination. Moreover, elastomeric materials are subject to mechanical wear, thus conferring limited service life to components constructed with them.

Additional types of threadless sealing interfaces for microfluidic devices are provided in U.S. Pat. No. 6,240,790 to Swedberg et al., which discloses various interconnect seals including the use of bosses and O-rings, direct/flat adhesive contact, sleeve fittings, and separate interconnects. These interconnect seals are disclosed for use with microanalysis devices preferably constructed by microfabricating a channel in the surface of a first substrate that mates with a second substrate in which a mirror-imaged channel has been fabricated to form a functional feature such as a separation channel. Certain of these sealing methods are ill suited for multi-use chromatography systems. For example, most O-rings are fabricated with soft materials that suffer from the same or similar drawbacks to the elastomeric materials discussed previously. O-rings are often ill-suited for repeated connection/disconnection cycles since they can come loose from their associated bosses or retention structures. In another example, the use of adhesives or material joining techniques utilizing direct bonding or ultrasonic welding usually provide permanent connections that may be incompatible with device designs that require temporary connections to enable periodic access to fluidic ports, such as for loading samples. If releasable (non-permanent) adhesives are used, the resulting interconnects typically pose chemical compatibility problems and may not seal against high operating pressures. Notably, Swedberg lacks details regarding specific channel configurations or other structures adapted to permit reliable fluidic interfaces at high operating pressures.

In light of the foregoing, it would be desirable to provide a re-useable fluidic interface to a microfluidic device capable of reliable, leak-free operation at high operating pressures without impairing operation of the microfluidic device. A desirable interface would also be threadless, permit rapid sealing and unsealing utility, and be characterized by minimal dead volume. Additionally, microfluidic devices to be used with the interface should preferably be easy to fabricate.

BRIEF DESCRIPTION OF THE DRAWINGS

FIG. 1A is a top view of a portion of a first microfluidic device including a fluidic port and a near-surface first channel in fluid communication with a second channel by way of an intermediate via, with the port, channels, and via being substantially aligned.

FIG. 1B is a side partial cross-sectional view of the microfluidic device of FIG. 1A and a portion of a fluidic seal depressed against the upper surface of the device, demonstrating impaired sealing engagement between the microfluidic device and the fluidic seal.

FIG. 1C is an end partial cross-sectional view of the microfluidic device and fluidic seal of FIG. 1B.

FIG. 1D is a top view of a portion of the microfluidic device of FIG. 1A, but with imperfect alignment between the port and the second channel.

FIG. 2A is a top view of a portion of a second microfluidic device including a fluidic port and a near-surface first channel in fluid communication with a second channel by way of an intermediate via, with the port, channels and via being substantially aligned, with the first channel being substantially narrower than the second channel, and with the fluidic port being substantially round in shape and having a diameter less than or equal to each of the length and width of the first channel.

FIG. 2B is a top view of the portion of the microfluidic device of FIG. 2A, but with imperfect alignment that severs fluid communication between the second channel and the fluidic port.

FIG. 3A is a top view of a portion of a third microfluidic device including a fluidic port and a near-surface second channel in fluid communication with a first channel by way of an intermediate via, with the port, channels, and via being substantially aligned, with the second channel being substantially narrower than the first channel, and with the fluidic port comprising an elongated shape disposed lengthwise substantially perpendicular to the second channel.

FIG. 3B is a side partial cross-sectional view of the microfluidic device of FIG. 3A and a portion of a fluidic seal depressed against the upper surface of the device, demonstrating improved sealing engagement between the microfluidic device and the fluidic seal.

FIG. 3C is an end partial cross-sectional view of the microfluidic device and fluidic seal of FIG. 3B.

FIG. 3D is a top view of the portion of the microfluidic device of FIG. 3A with imperfect alignment between the first channel and the fluidic port that fails to significantly impair fluid communication between the first channel and fluidic port.

FIG. 3E is an expanded top view of the microfluidic device portion illustrated in FIG. 3A.

FIG. 4 is a top view of a multi-layer microfluidic device containing twenty-four separation columns suitable for performing pressure-driven liquid chromatography, the device embodying multiple near-surface channel structures resembling the channel portions illustrated in FIG. 3A.

FIG. 5C is an exploded perspective view of a third portion, including the seventh through ninth layers, of the microfluidic device shown in FIG. 4.

FIG. 6 is a schematic of a system for performing high throughput pressure-driven liquid chromatography utilizing a microfluidic device such as illustrated in FIGS. 4 and 5A–5E.

Figure 5A:
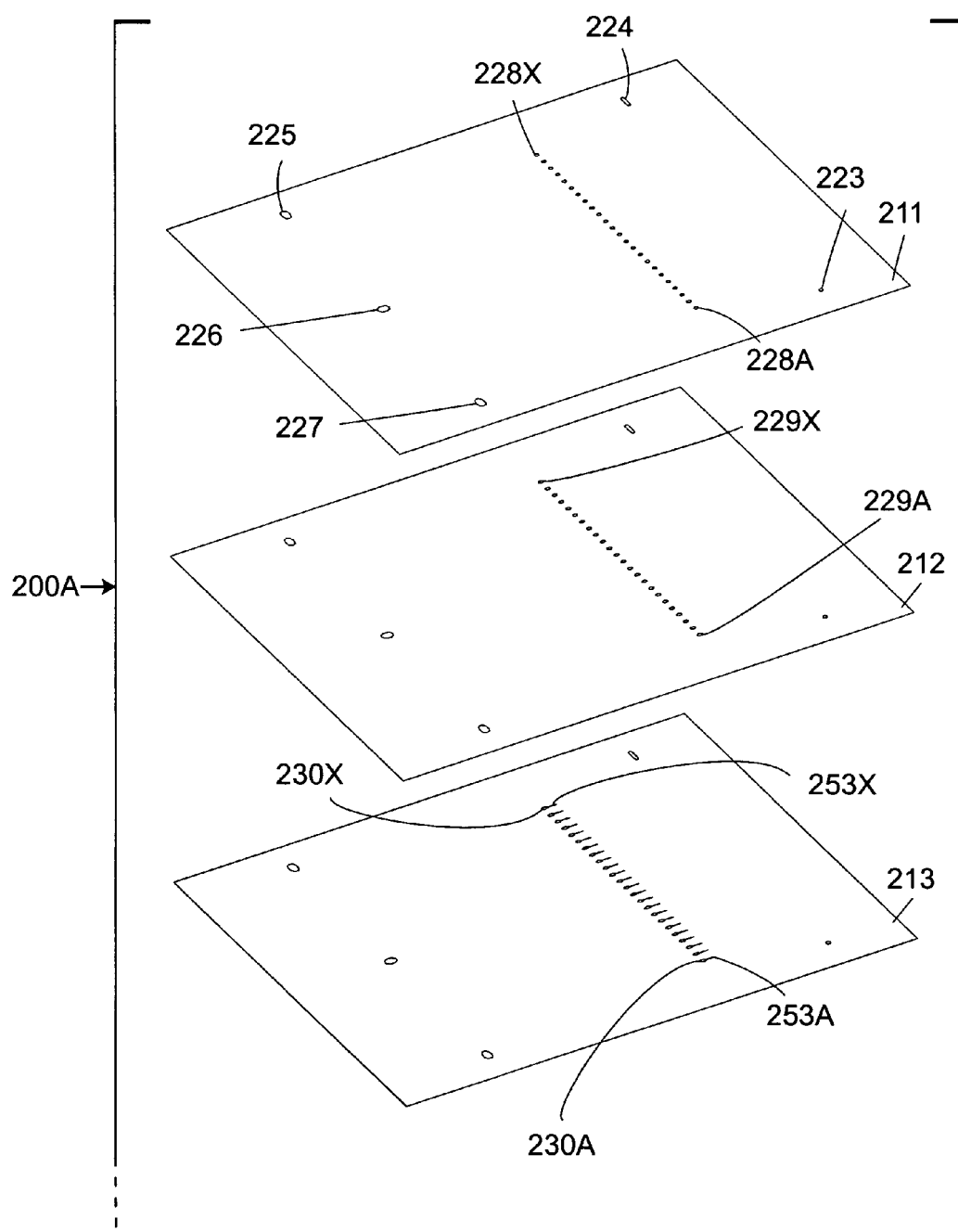
FIG. 5A is an exploded perspective view of a first portion, including the first through third layers, of the microfluidic device shown in FIG. 4.

None of the figures are drawn to scale unless indicated otherwise. The size of one figure relative to another is not intended to be limiting, since certain figures and/or features may be expanded to promote clarity in the description.

DETAILED DESCRIPTION OF PREFERRED EMBODIMENTS

Definitions

The term "collapse" as used herein refers to a substantially complete closure or blockage of a fluidic channel, such as may be caused by compressing the upper and lower boundaries of a channel together.

The terms "column" or "separation column" as used herein are used interchangeably and refer to a region of a fluidic device that contains stationary phase material and is adapted to perform a separation process.

The term "depth" as used herein with regard to a microfluidic channel structure refers to the distance between the outer surface of a microfluidic device and the parallel channel surface nearest to the outer surface. For example, if depth of a channel is measured relative to an upper surface of a microfluidic device, the depth is equal to the distance between the upper boundary of the channel and the upper (outer) surface of the device.

The term "elastomer" as used herein refers to a polymeric material that is crosslinked to form a network structure, and characterized by the ability to return to its original dimensions after the removal of external stresses.

The term "fluidic distribution network" refers to an interconnected, branched group of channels and/or conduits capable of or adapted to divide a fluid stream into multiple substreams.

The term "frit" refers to a liquid-permeable material adapted to retain stationary phase material within a separation column.

The term "microfluidic" as used herein refers to structures or devices through which one or more fluids are capable of being passed or directed and having at least one dimension less than about 500 microns.

The term "parallel" as used herein refers to the ability to concomitantly or substantially concurrently process two or more separate fluid volumes, and does not necessarily refer to a specific channel or chamber structure or layout.

The term "plurality" as used herein refers to a quantity of two or more.

The term "stencil" as used herein refers to a material layer or sheet that is preferably substantially planar through which one or more variously shaped and oriented portions have been cut or otherwise removed through the entire thickness of the layer, and that permits substantial fluid movement within the layer (e.g., in the form of channels or chambers, as opposed to simple through-holes for transmitting fluid through one layer to another layer). The outlines of the cut or otherwise removed portions form the lateral boundaries of microstructures that are formed when a stencil is sandwiched between other layers such as substrates and/or other stencils.

Microfluidic Devices Generally

Traditionally, microfluidic devices have been fabricated from rigid materials such as silicon or glass substrates using surface micromachining techniques to define open channels and then affixing a cover to a channel-defining substrate to enclose the channels. There now exist a number of well-established techniques for fabricating microfluidic devices, including machining, micromachining (for example, photolithographic wet or dry etching), micromolding, LIGA, soft lithography, embossing, stamping, surface deposition, and/or combinations thereof to define apertures, channels or chambers either in one or more surfaces of a material or penetrating through a material.

A preferred method for constructing microfluidic devices utilizes stencil fabrication, which involves the use of at least one stencil layer or sheet defining one or more microfluidic channels and/or other microstructures, with the at least one stencil layer disposed (preferably laminated) between outer or cover layers. One or both outer/cover layers preferably define at least one fluidic port to permit fluids to be supplied to or received from the device. As noted previously, a stencil layer is preferably substantially planar and has a channel or chamber cut through the entire thickness of the layer to permit substantial fluid movement within that layer.

Various means may be used to define such channels or chambers in stencil layers. For example, a computer-controlled plotter modified to accept a cutting blade may be used to cut various patterns through a material layer. Such a blade may be used either to cut sections to be detached and removed from the stencil layer, or to fashion slits that separate regions in the stencil layer without removing any material. Alternatively, a computer-controlled laser cutter may be used to cut portions through a material layer. While laser cutting may be used to yield precisely dimensioned microstructures, the use of a laser to cut a stencil layer inherently involves the removal of some material. Further examples of methods that may be employed to form stencil layers include conventional stamping or die-cutting technologies, including rotary cutters and other high throughput auto-aligning equipment (sometimes referred to as converters). The above-mentioned methods for cutting through a stencil layer or sheet permits robust devices to be fabricated quickly and inexpensively compared to conventional surface micromachining or material deposition techniques that are conventionally employed to produce microfluidic devices.

After a portion of a stencil layer is cut or removed, the outlines of the cut or otherwise removed portions form the lateral boundaries of microstructures that are completed upon sandwiching a stencil between substrates and/or other stencils. The thickness or height of the microstructures such as channels or chambers can be varied by altering the thickness of the stencil layer, or by using multiple substantially identical stencil layers stacked on top of one another. When assembled in a microfluidic device, the top and bottom surfaces of stencil layers mate with one or more adjacent layers (such as stencil layers or substrate layers) to form a substantially enclosed device, typically having at least one inlet port and at least one outlet port.

A wide variety of materials may be used to fabricate microfluidic devices having sandwiched stencil layers, including polymeric, metallic, and/or composite materials, to name a few. Various preferred embodiments utilize porous materials including filtration media. Substrates and stencils may be substantially rigid or flexible. Selection of particular materials for a desired application depends on numerous factors including: the types, concentrations, and residence times of substances (e.g., solvents, reactants, and products) present in regions of a device; temperature; pressure; pH; presence or absence of gases; and optical properties. For instance, particularly desirable polymers include polyolefins, more specifically polypropylenes, and vinyl-based polymers.

Various means may be used to seal or bond layers of a device together. For example, adhesives may be used. In one embodiment, one or more layers of a device may be fabricated from single- or double-sided adhesive tape, although other methods of adhering stencil layers may be used. Portions of the tape (of the desired shape and dimensions) can be cut and removed to form channels, chambers, and/or apertures. A tape stencil can then be placed on a supporting substrate with an appropriate cover layer, between layers of tape, or between layers of other materials. In one embodiment, stencil layers can be stacked on each other. In this embodiment, the thickness or height of the channels within a particular stencil layer can be varied by varying the thickness of the stencil layer (e.g., the tape carrier and the adhesive material thereon) or by using multiple substantially identical stencil layers stacked on top of one another. Various types of tape may be used with such an embodiment. Suitable tape carrier materials include but are not limited to polyesters, polycarbonates, polytetrafluoroethlyenes, polypropylenes, and polyimides. Such tapes may have various methods of curing, including curing by pressure, temperature, or chemical or optical interaction. The thickness of these carrier materials and adhesives may be varied.

Device layers may be directly bonded without using adhesives to provide high bond strength (which is especially desirable for high-pressure applications) and eliminate potential compatibility problems between such adhesives and solvents and/or samples. For example, in one embodiment, multiple layers of 7.5-mil (188 micron) thickness "Clear Tear Seal" polypropylene (American Profol, Cedar Rapids, Iowa) including at least one stencil layer may be stacked together, placed between glass platens and compressed to apply a pressure of 0.26 psi (1.79 kPa) to the layered stack, and then heated in an industrial oven for a period of approximately five hours at a temperature of 154° C. to yield a permanently bonded microstructure well-suited for use with high-pressure column packing methods. In another embodiment, multiple layers of 7.5-mil (188 micron) thickness "Clear Tear Seal" polypropylene (American Profol, Cedar Rapids, Iowa) including at least one stencil layer may be stacked together. Several microfluidic device assemblies may be stacked together, with a thin foil disposed between each device. The stack may then be placed between insulating platens, heated at 152° C. for about 5 hours, cooled with a forced flow of ambient air for at least about 30 minutes, heated again at 146° C. for about 15 hours, and then cooled in a manner identical to the first cooling step. During each heating step, a pressure of about 0.37 psi (2.55 kPa) is applied to the microfluidic devices. Additional bonding methods are disclosed in commonly assigned U.S. Patent Application Publication No. 2003/0106799, which is hereby incorporated by reference. In a preferred embodiment, an adhesiveless microfluidic device is adapted to withstand a fluidic supply pressure of at least about 100 pounds per square inch; more preferably at least about 250 pounds per square inch; and still more preferably at least about 500 pounds per square inch.

Notably, stencil-based fabrication methods enable very rapid fabrication of devices, both for prototyping and for high-volume production. Rapid prototyping is invaluable for trying and optimizing new device designs, since designs may be quickly implemented, tested, and (if necessary) modified and further tested to achieve a desired result. The ability to prototype devices quickly with stencil fabrication methods also permits many different variants of a particular design to be tested and evaluated concurrently.

In addition to the use of adhesives and the adhesiveless bonding method discussed above, other techniques may be used to attach one or more of the various layers of microfluidic devices useful with the present invention, as would be recognized by one of ordinary skill in attaching materials. For example, attachment techniques including ultrasonic, thermal, chemical, or light-activated bonding steps; mechanical attachment (such as using clamps or screws to apply pressure to the layers); combinations thereof; and/or other equivalent joining methods may be used.

Near-Surface Channel Structures

A simple method for threadlessly interfacing with a microfluidic device involves pressing an external seal plate (or equivalent sealing member) against an outer surface of the device at a high contact pressure. One difficulty associated with this approach, however, is that the contact pressure required to prevent leakage of high-pressure fluids along the interface may be so high that it deforms a portion of one or more outer layers into one or more channels within the microfluidic device. This deformation may lead to the formation of a reduced contact pressure region or gap between the seal plate and the deformed portion of the outer layer, and further lead to occlusion of the affected channel(s) disposed within the device. If excessively high contact pressures are used in an attempt to prevent leakage along the fluidic interface, then the microfluidic device may be rendered inoperable due to the occlusion of the affected channel(s).

Examples of a microfluidic device and threadless fluidic interface subject to the above-described limitations are illustrated in FIGS. 1A–1D. FIG. 1A is a top view of a portion of a first microfluidic device 100 having a fluidic port 16 defined in a first (outer) device layer 101 (as illustrated in FIG. 1B), a first "near-surface" microfluidic channel 14 defined in a second device layer 102, a via 12 defined in another device layer, and a second microfluidic channel defined in yet another device layer. As illustrated in FIGS. 1B–1C, the device 100 includes at least six device layers 101–106. In one embodiment, each device layer 101–106 is fabricated with a polyolefin material having a thickness of about 7.5 mils (0.19 mm), the port 16 has a diameter of about 33 mils (0.84 mm), the first channel 14 has a width of about 22 mils (0.56 mm), the via 12 has a diameter of about 45 mils (1.14 mm), and the second channel 10 has a width of about 33 mils (0.84 mm). FIGS. 1B–1C also illustrate a portion of a fluidic seal 130 adapted to mate with the upper layer 101 of the device 100. The seal 130 defines a protruding boss 132, preferably annular in shape, that surrounds a fluidic passage 134 defined in the seal 130. Either or both of the device 100 and seal 130 may be depressed against the other to elevate the contact pressure therebetween. In the interest of preventing the leakage of high pressure fluid between the device 100 and the seal 130, the contact pressure is preferably at least about ten pounds per square inch, and more preferably at least about one hundred pounds per square inch. At such elevated contact pressures, however, the boss 132 tends to locally deform a portion 101A of the upper layer 101 into the near-surface channel 14. In other words, a portion 101A of the upper layer 101 is insufficiently well-supported by the walls of the adjacent channel 14 to resist sag or even collapse of the "roof" 101A of the channel 14 due to transmission of the contact pressure. Not only can this deformation substantially occlude the channel 14, but also it tends to establish a low contact pressure region or gap 109 between the upper layer 101 and the seal 130 that may permit the escape of pressurized fluid (not shown) contained within the device 100 and/or conduit 134.

One method for reducing contact-pressure-induced deformation of a portion of the upper layer into a near-surface channel of a microfluidic device is to alter the dimensions of the near-surface channel. Applicants have found that adjusting the width of the near-surface channel to preferably less than about two times its depth relative to the outer surface—more preferably less than or equal to the depth—reduces deformation of the upper layer sufficiently to prevent leakage at desirable internal fluidic operating pressures while preventing contact-pressure-induced occlusion of the near-surface channel. In other words, the near-surface channels should be narrow enough to render it difficult for the material above the channel to flex into them.

In the example shown in FIGS. 1A–1D, the ratio of width to depth for the near-surface channel 14 was almost three. In the examples shown in FIGS. 2A–2B and 3A–3E, the width of each of the near-surface channels 24, 34 is nearly equal to their depth. For example, in FIGS. 2A–2B, the fluidic port 26 has a diameter of about 7 mils (0.18 mm) and the near-surface channel 24 has a width of about 7 mils (0.18 mm), with the via 22 and second channel 20 being unchanged relative to the previous example with a diameter of about 45 mils (1.14 mm) and a width of about 33 mils (0.84 mm), respectively. In another example illustrated in FIGS. 3A–3E, a microfluidic device 110 fabricated with multiple device layers 111–116 includes a fluidic port 36 having a diameter of about 7 mils (0.18 mm), a near-surface channel 34 having a width of about 7 mils (0.18 mm), and a via 32 and second channel 30 having equivalent dimensions to the corresponding structures in the previous example (i.e., a diameter of about 45 mils (1.14 mm) and a width of about 33 mils (0.84 mm), respectively. The effect of the reduced width of the near surface channel 34 on resisting deformation of the upper layer in the presence of a high contact pressure is illustrated in FIGS. 3B–3C. Despite having the same fluidic sealing element 130 with a raised boss 132 depressed against (and substantially into) the upper layer 111 of the device 110 at the same high contact pressure, only a very small deformation 111A results in the upper layer 111 adjacent to the boss 132. As a result, no substantial low contact pressure region or gap is formed between the seal 130 and device 110 (compared to the low pressure region or gap 109 illustrated in FIG. 1B), and the channel 34 remains substantially unobstructed. Systems embodying sealing interfaces of this type are well-suited for resisting leakage at a fluidic supply pressure of preferably at least about 100 pounds per square inch, more preferably at least about 250 pounds per square inch.

In addition to enhancing structural integrity, the reduced width of the near-surface channels 24 and 34 may provide a further benefit in the form of reduced dead volume. In analytical applications such as liquid chromatographic separation, it is desirable to minimize the volume of a fluid flow path downstream of a separation region (e.g., chromatographic separation column) to decrease the amount of detrimental post-column band broadening. As a result, reduced width near-surface channels embodying the width-to-depth aspect ratios described herein may be particularly useful when provided at the outlets of microfluidic separation column devices.

Fault-Tolerant Flow Path Design

Although the two devices illustrated in FIGS. 2A–2B and FIGS. 3A–3E both have similarly positive structural integrity characteristics due to the similar (i.e., the same) width-to-depth aspect ratios of their near-surface channels 24, 34, the device configuration illustrated in FIGS. 2A–2B is less preferred due to its impaired ability to tolerate variations in alignment between layers during device fabrication. Although FIG. 2A and FIG. 2B illustrate the same device, the microstructures 20, 22, 24, 26 are aligned perfectly in FIG. 2A, while FIG. 2B illustrates misalignment between the adjacent layers defining the fluidic port 26 and near-surface channel 24. The result of this misalignment is a lack of fluid communication between the port 26 and channel 24, thus breaking continuity in a fluid flow path through the device. As shown in FIG. 1D, such a discontinuity would not result from similar misalignment between layers in the first device 100 due to the large width of the near-surface channel 14; however, as described previously, the device 100 is not well-suited for operation with threadless fluidic seals engaged to the device 100 at high contact pressures.

A preferred design that provides enhanced structural integrity in conjunction with high-contact-pressure fluidic sealing interfaces while also providing enhanced tolerance against inter-layer misalignment is the device 110 illustrated in FIGS. 3A–3E. As shown in FIG. 3D, slight misalignment between the layer defining the fluidic 36 and the adjacent layer defining the near-surface narrow channel 34 does not result in discontinuity in the fluid flow path including these structures. As shown most clearly in FIG. 3E, the fluidic port 36 is elongated in shape, with a length 36B that is much greater than its width 36A. Additionally, the fluidic port 36 is disposed lengthwise along a first axis X, whereas the near-surface channel 34 is disposed lengthwise along a second axis Y that is substantially perpendicular to the first axis X. As a result, the elongated port 36 is disposed lengthwise substantially perpendicular to the length of the near-surface channel 34, with the port 36 overlapping the channel 34. Ideal alignment between the elongated port 36 and near-surface channel 34 is illustrated in FIGS. 3A and 3E; but as shown in FIG. 3D, the elongated port 36 and channel 34 can tolerate significant inter-layer misalignment without detrimentally affecting fluid flow capability. Additionally, as compared to the wider near-surface channel 14 and larger circular port 16 of the previous device 100, the corresponding narrow near-surface channel 34 and transverse elongated port 36 of the present device 110 are characterized by substantially lower total volume. If this narrowed near-surface channel 34 and elongated port 36 are used at the outlet of a separation device, their reduced overall volume reduces the potential for detrimental band broadening.

The fluidic port 36 may be formed in various elongated shapes. While the port 36 illustrated in FIG. 3E resembles a rectangle with rounded corners, alternative elongated shapes include rectangles, ovals, triangles, and trapezoids.

Microfluidic Analytical Device with Narrowed Near-Surface Channel Structures

Figure 5B:
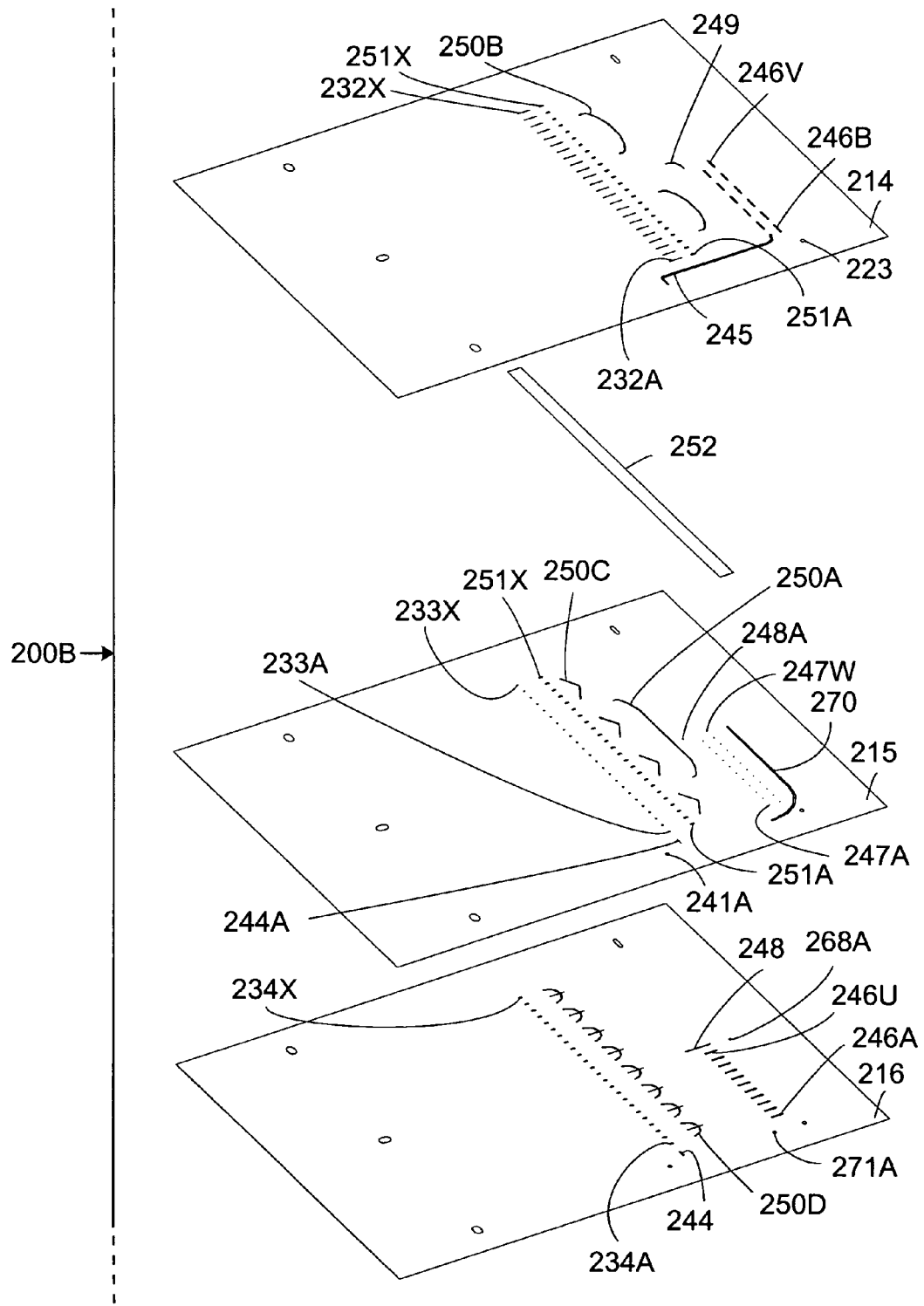
FIG. 5B is an exploded perspective view of a second portion, including the fourth through sixth layers, of the microfluidic device shown in FIG. 4.
Figure 5D:
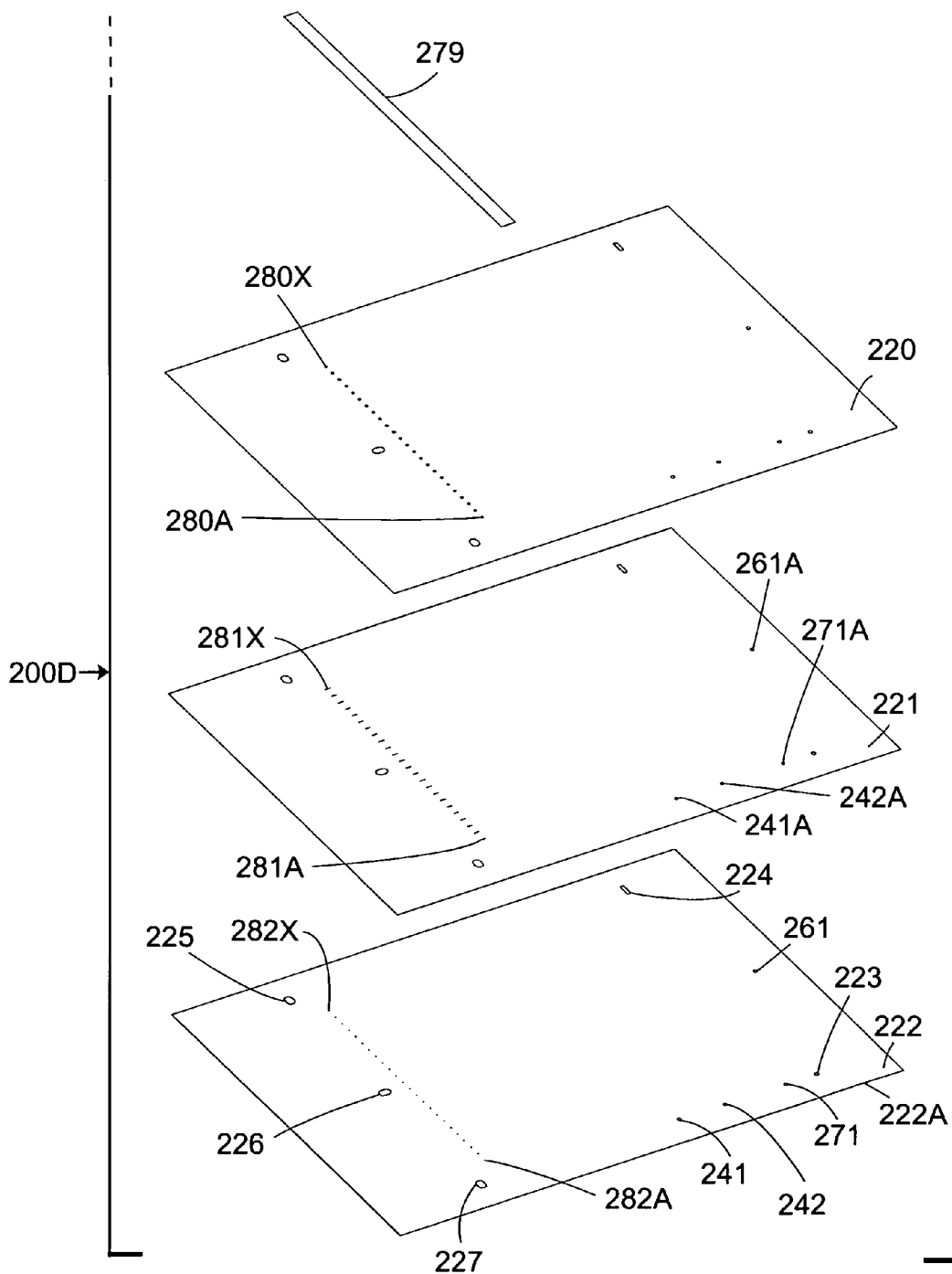
FIG. 5D is an exploded perspective view of a fourth portion, including the tenth through twelfth layers, of the microfluidic device shown in FIG. 4.
Figure 5E:
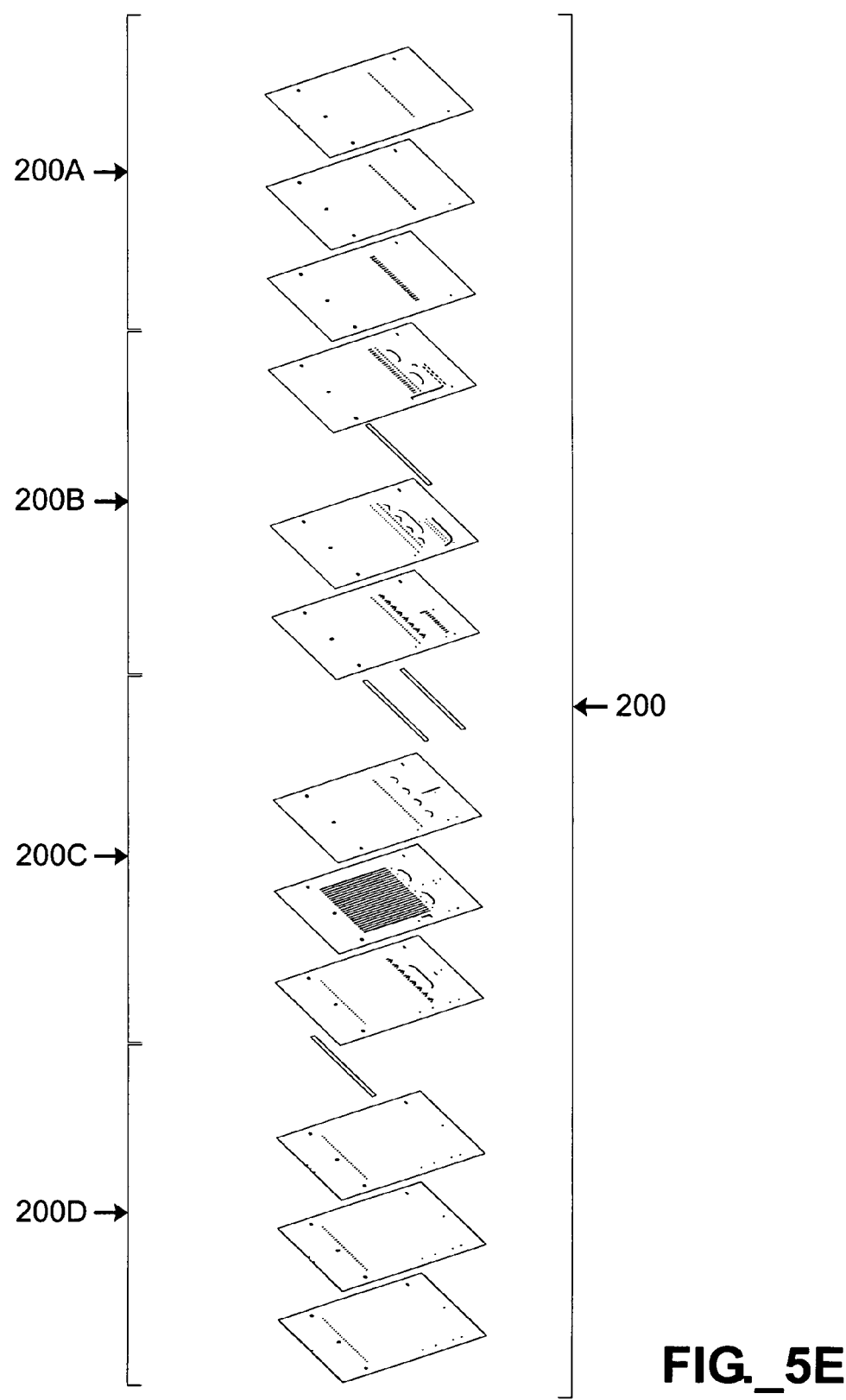
FIG. 5E is a reduced scale composite exploded perspective view of the microfluidic device illustrated in FIGS. 4 and 5A–5D.

In one example, the above-described interface may be utilized with a microfluidic analytical device adapted to perform high performance liquid chromatography at elevated operating pressures. One embodiment of such a device 200 is illustrated in FIGS. 4 and 5A–5E. The device 200 includes twenty-four parallel separation channels (or "columns") 239A–239X containing stationary phase material. The device 200 is constructed with twelve device layers 211–222, including multiple stencil layers 213–219, 221 and two outer or cover layers 211, 222. Each of the twelve device layers 211–222 defines five alignment holes 223–227, which may be used in conjunction with external pins (not shown) or equivalent structures to aid in aligning the layers during fabrication or may be used with an external interface (not shown) to position the device 200 for performing a packing process or for operating the device 200.

Preferably, the device 200 is constructed with materials selected for their compatibility with chemicals typically utilized in performing high performance liquid chromatography, including, water, methanol, ethanol, isopropanol, acetonitrile, ethyl acetate, dimethyl sulfoxide, and mixtures thereof. Specifically, the materials of the device should be substantially non-absorptive of, and substantially non-degrading when placed into contact with, such chemicals. Suitable device materials include polyolefins—such as polypropylene, polyethylene, and copolymers thereof—which have the further benefit of being substantially optically transmissive so as to aid in performing quality control routines (including checking for fabrication defects) and in ascertaining operational information about the device or its contents. For example, each device layer 211–222 may be fabricated from 7.5 mil (188 micron) thickness cast unoriented polypropylene (Copol International Ltd., Nova Scotia, Canada).

The first device layer 211 defines twenty-four sample inlet ports 228A–228X, each being oval-shaped with nominal dimensions of 65×50 mils (1.7×1.3 mm). The second device layer 212 defines twenty-four corresponding sample vias 229A–229X, each also being oval-shaped with nominal dimensions of 80×50 mils (2.0×1.3 mm). The third device layer 213 defines twenty-four sample wells 230A–230X (each being oval in shape and having nominal dimensions of 100×50 mils (2.5×. 1.3 mm)) and each having an associated mobile phase loading channel segment 253A–253X. When the device 200 is assembled and each corresponding first layer port (e.g., 228A), second layer via (e.g., 229A) and third layer well (e.g., 230A) is aggregated, the combination serves as an injection pit for receiving a sample. Thus, the device 200 may receive up to twenty-four different samples simultaneously—namely, a different sample through each sample inlet port 228A–228X. An external seal plate (not shown) is preferably pressed against the device 200 after sample loading is complete to permit the samples to be forced through the separation columns 239A–239X.

The fourth through sixth device layers 214–216 define a mobile phase distribution network 250 (inclusive of multiple channel elements 250A–250D) adapted to split a supply of mobile phase solvent among the twenty-four channel loading segments 253A–253X and ultimately the separation columns 239A–239X. In a preferred embodiment, the various channels of the mobile phase distribution network have widths of about 10 mils (0.25 mm). Upstream of the mobile phase distribution network 250, the fourth through sixth layers 214–216 further define mobile phase channels 248, 249 and structures for mixing mobile phase solvents, including a long mixing channel 245, wide slits 244, 244A, alternating channel segments 246A–246V (defined in the fourth and sixth layers 214, 216) and vias 247A–247W (defined in the fifth layer 215). In a preferred embodiment, the mixing elements (including channel 245 and segments 246A–246V) each have a nominal dimension (e.g., width) of about 20 mils (0.51 mm). Each of the fourth and fifth layers 214, 215 also define twenty-four solvent vias 251A–251X adjacent to an intermediate frit 252, with the fourth layer 214 further defining twenty-four sample/solvent channel segments 232A–232X. Additionally, the fifth and sixth layers 215, 216 define twenty-four sample/solvent vias 233A–233X, 234A–234X, respectively, and the fifth layer 215 defines an additional mobile phase via 248A.

Preferably, the device is adapted to retain particulate-based stationary phase material such as, for example, silica-based particulate to which functional groups (e.g., hydrophobic C-18 or other carbon-based groups) have been added. One difficulty associated with conventional microfluidic devices has been retaining small particulate matter within specific areas during operation at elevated pressures. The present device 200 overcomes this difficulty by utilizing liquid-permeable porous frits (e.g., frits 235, 269, 279) each having an average pore size that is smaller than the average particle size of the particulate-based stationary phase material. For example, each frit 235, 269, 279 may comprise a strip of porous material such as 1-mil thickness Celgard 2500 polypropylene membrane (55% porosity, 0.209×0.054 micron pore size, Celgard Inc., Charlotte, N.C.) and inserted into the appropriate regions of the stacked device layers 211–222 before the layers 211–222 are laminated together. Notably, the additional frit 252 disposed adjacent to the mobile phase distribution network 250 does not serve to retain stationary phase material but may be fabricated from the same material as the other frits (i.e., the sample injection frit 235, vent frit 269, and column outlet frit 279).

Preferably, an adhesiveless bonding method such as one of the methods described previously herein is used to interpenetrably bond the device layers 211–222 (and frits 235, 252, 269, 279) together. Such methods are desirably used to promote high bond strength (e.g., to withstand operation at high internal pressures of preferably at least about 100 psi (690 kPa), more preferably at least about 500 psi (3450 kPa)) and to prevent undesirable interaction between any bonding agent and solvents and/or samples to be supplied to the device 200.

While the device 200 includes twenty-four sample inlet ports 228A–228X defined in the first (top) layer 211, additional fluidic connections to the device 200 are made through ports defined in the twelfth (bottom) layer 222, namely: multiple mobile phase inlet ports 241, 242, a slurry inlet port 261, and a vent (outlet) port 271. Vias corresponding to these bottom ports 241, 242, 261, 271 are defined in multiple device layers to communicate fluids to or from the interior of the device 200, such as: first mobile phase solvent vias 241A defined in each of the fifth through eleventh layers 215–221; second mobile phase solvent vias 242A defined in each of the ninth through eleventh layers 219–221; slurry inlet vias 261A defined in each of the eighth through eleventh layers 218–221; and vent ports 271A defined in each of the sixth through eleventh layers 216–221.

A convenient method for packing stationary phase material within the separation channels 239A–239X is to provide it in the form of a slurry (i.e., particulate material mixed with a solvent such as acetonitrile). Following assembling and bonding of the device layers 211–222, slurry is supplied to the device 200 by way of the slurry inlet port 261, slurry vias 261A, channel segment 262, and a slurry distribution network 264 (inclusive of channel structures 264A–264D defined in the seventh through ninth layers 217–219). During the slurry packing process, the device 200 is preferably retained within an external packing manifold (not shown). In a preferred embodiment, the channel segment 262 has a width of about 30 mils (0.76 mm) and each portion of the slurry distribution network 264 has a width of about 10 mils (0.25 mm). The vent port 271 is preferably in fluid communication with a slurry feed channel 262 to provide a path for air bubbles or other compressible fluids to escape the device 200 upon pressurization. In support of these functions, the seventh device layer 217 defines a slurry channel 262, a vent via 268A, four medium forked channels 264C, twenty-four sample/solvent vias 236A–236X, and a slit-shaped mobile phase via 244 (in fluid communication with a mobile phase feed channel 243 and widened terminus 243A defined in the eighth layer 218). The eighth device layer 218 defines two vent vias 266, 268A, a slurry via 263, two large forked channels 264B, eight slurry packing vias 265A–265H, and twenty-four separation columns 239A–239X (nominally about 30 mils (0.76 mm) wide with an effective length of about 8 cm in a preferred embodiment) each having an associated narrow upstream portion 238A–238X (nominally about 10 mils (0.25 mm) wide in a preferred embodiment) and wider upstream terminus 237A–237X. The ninth layer 219 defines a vent channel segment 267, a very large forked channel 264A, eight small forked channels 264D each having three outlets, and twenty-four eluate vias 278A–278X.

In the aggregate, the very large, large, medium, and small forked channels 264A–264D form a slurry distribution network that communicates slurry from a single inlet (e.g., slurry inlet port 261) to the twenty-four separation channels 239A–239X. As particulate-containing slurry is added to the separation channels 239A–239X in a packing process, the particulate stationary phase material is retained within the separation channels 239A–239X by one column outlet frit 279 and by one sample injection frit 235, while the liquid portion of the slurry exiting the device 200 through the column outlet ports 281A–281X and the vent port 271. Note that the vent frit 269 serves to further prevent particulate material from unpacking or escaping the device 200 through the vent channel 270 or associated vent port 271. After stationary phase material is packed into the columns 239A–239X, a sealant (preferably substantially inert such as UV-curable epoxy) may be added to the slurry inlet port 261 to prevent the columns 239A–239X from unpacking during operation of the device 200. The addition of sealant should be controlled to prevent blockage of the vent via 266 and related vent structures including the vent channel 270. Further details regarding column packing methods are provided in commonly assigned U.S. Patent Application Publication no. 2003/0150806 entitled "Separation column devices and fabrication methods," which is hereby incorporated by reference.

As an alternative to using packed particulate material, porous monoliths may be used as the stationary phase material. Generally, porous monoliths may be fabricated by flowing a monomer solution into a channel or conduit, and then activating the monomer solution to initiate polymerization. Various formulations and various activation means may be used. The ratio of monomer to solvent in each formulation may be altered to control the degree of porosity of the resulting monolith. A photoinitiator may be added to a monomer solution to permit activation by means of a lamp or other radiation source. If a lamp or other radiation source is used as the initiator, then photomasks may be employed to localize the formation of monoliths to specific areas within a fluidic separation device, particularly if one or more regions of the device body are substantially optically transmissive. Alternatively, chemical initiation or other initiation means may be used. Numerous recipes for preparing monolithic columns suitable for performing chromatographic techniques are known in the art. In one embodiment a monolithic ion-exchange column may be fabricated with a monomer solution of about 2.5 ml of 50 millimolar neutral pH sodium phosphate, 0.18 grams of ammonium sulfate, 44 microliters of diallyl dimethlyammonium chloride, 0.26 grams of methacrylamide, and 0.35 grams of piperazine diacrylamide.

Each of the tenth and eleventh device layers 220–221 define several vias 241A, 242A, 261A, 271A in fluid communication with corresponding ports 241, 242, 261, 271 defined in the twelfth device layer 222. Downstream of the separation columns 239A–239X, the tenth layer 220 defines twenty-four column outlet vias 280A–280X that are in fluid communication with twenty-four narrow near-surface channel segments 281A–281X defined in the eleventh layer 221 and, in turn, twenty-four elongated eluate (outlet) ports 282A–282X defined in the twelfth layer 222 and disposed lengthwise substantially perpendicular to the direction of the adjacent narrow channel segments 281A–281X. Notably, the combination of each outlet via 280A–280X, narrow near-surface channel segment 281A–281X, and transversely disposed elongated outlet port 282A–282X corresponds to the via 32, narrow segment 34, and transverse port 36 illustrated and described in connection with FIGS. 3A–3E to provide a fault-tolerant near-surface channel structure with low dead volume that is particularly well-suited for use with threadless external seals operated at high contact pressures. In a preferred embodiment, each device layer 211–222 has a thickness of about 7.5 mils (190 microns), each narrow channel segment 281A–281X measures approximately 7 mils×85 mils (178 microns×2.2 mm), and each transverse port 282A–282X measures approximately 7 mils×25 mils (178 microns×640 microns). Dimensional tolerances of roughly 1 mil (25 microns) may be expected if the device layers are patterned by laser cutting.

Utilizing the dimensions of this preferred embodiment, each narrow channel segment 281A–281X is disposed at a depth of about 7.5 mils (190 microns) (equal to the thickness of the twelfth layer 222) relative to the outer (e.g., lower) surface 222A of the device 200; thus, at a channel width of about 7 mils (178 microns), the width of each narrow channel segment 281A–281X is well less than about two times its depth—in fact, the width of each narrow channel segment 281A–281X is closer to parity with its depth relative to the outer surface 222A. Ensuring that the width of each narrow channel segment 281A–281X is less than about two times, or more preferably, less than or about equal to, the depth of each such segment 281A–281X helps to promote reliable threadless interconnection between the device 200 and external sealing components (e.g., such as the seal element 130 illustrated and described in connection with FIGS. 3B–3C) because the likelihood of significant localized deformation or collapse of the near-surface channel segments is dramatically reduced. In other words, careful selection of the ratio of width of the channel segments 281A–281X to their depth relative to the adjacent outer surface 222A permits external sealing components to be pressed against the lower surface 222A of the device 200 at high contact pressures without concern that a portion of the lower layer 222 will deflect into any channel segment 281A–281X and either (1) open an undesirable fluid flow path or gap between the sealing component and the outer surface 222A (e.g., the gap 109 as illustrated in FIG. 1B) or (2) substantially occlude the channel segment 281A–281X (such as the channel 14 occluded by a portion 101A of the outer layer 101 illustrated in FIG. 1B).

After the various layers of the device 200 have been laminated or otherwise joined together, and after stationary phase material has been supplied to the separation channels 239A–239X, the device 200 may be readied for operation by supplying one or more mobile phase solvents through the mobile phase inlet ports 241, 242 while the sample inlet ports 228A–228X are temporarily covered with an external seal (not shown). The mobile phase solvents may be optionally pre-mixed upstream of the device 200 using a conventional micromixer (not shown) and then supplied to the device though only a single mobile phase inlet port 241, 242 of the two available ports 241, 242. If it is desired to provide mixing utility with the device 200, then the multiple solvents may be conveyed through several vias 241A, 242A to the mixing elements. A first solvent stream is supplied to the end of the long mixing channel 245, while another other solvent stream is supplied to a short mixing segment 243 that overlaps the mixing channel 245 through slit-shaped vias 244, 244A defined in the fifth through seventh device layers 215–217. One solvent is layered atop the other across the entire width of the long mixing channel 246 to promote diffusive mixing as the fluids flow through the "overlap mixing" channel 245, which has a nominal width of about 20 mils (0.51 mm) in a preferred embodiment. To ensure that the solvent mixing is complete, however, the combined solvents also flow through a second mixer of a different type composed of alternating channel segments 246A–246V and vias 247A–247W. The net effect of forcing the solvents through these alternating segments 246A–246V and vias 247A–247W is to cause the combined solvent stream to contract and expand repeatedly, augmenting mixing between the constituents of the two solvent streams initially supplied to the device 200. The mixed solvents are supplied through channel segments 248, 249 to the distribution network 250 inclusive of forked channels 250A–250D. Each of the eight smaller forked channels 250D is in fluid communication with three of twenty-four sample loading channel segments 253A–253X. Additionally, each sample loading channel segment 253A–253X is in fluid communication with a different sample loading port 228A–228X by way of sample vias 229A–229X. To prepare the device 200 for sample loading, solvent flow is temporarily interrupted, an external interface (not shown) previously covering the sample loading ports 228A–228X is opened, and samples are supplied through the sample ports 228A–228X and the sample loading vias 229A–229X into the sample wells 230A–230X. Following sample loading, the sample loading ports 228A–228X are again sealed (e.g., with an external interface) and solvent flow is re-initiated to carry the samples onto the separation columns 239A–239X defined in the eighth layer 218.

While the bulk of the sample and solvent that is supplied to each column 239A–239X travels downstream through the columns 239A–239X in the direction of the outlet ports 282A–282X, a small split portion of each sample and solvent travels upstream through the columns 239A–239X in the direction of the stationary phase distribution network 264 and the vent port 270. That is, the split portions of sample and solvent from each column that travel upstream are consolidated by way of the slurry distribution network 264 (also containing packed stationary phase material to provide a high impedance to fluid flow) into a single waste stream that may flow through the vent port 270 to exit the device 200. One benefit of providing the vent port 270 in fluid communication with the columns 239A–239X is to permit air bubbles introduced during atmospheric pressure injection to escape the device 200 without worry of unpacking the slurry network 264 due to the presence of the frit 269. Providing a bubble escape path prevents pockets of compressed air (bubbles) from expanding upon release of the sample loading seal (not shown), which could lead to undesirable cross-contamination of samples from one separation run to the next and/or alter solvent gradient conditions from one column to another. In other words, since the device 200 is designed for atmospheric on-column sample injection, if there existed no means for venting the stationary phase distribution network 264 upstream of the sample injection ports 228A–228X, then the stationary phase network 264 would provide a stagnant "pocket" capable of retaining air bubbles, samples, and/or mobile phase solvents, and the process of depressurizing this pocket after pressurization would cause its contents to expand or surge into the sample injection wells 230A–230X and/or columns 239A–239X. Providing the vent 270 eliminates these problems.

Either isocratic separation (in which the mobile phase composition remains constant) or, more preferably, gradient separation (in which the mobile phase composition changes with time) may be performed with the device 200. If multiple separation columns are provided in a single integrated device (such as the device 200) and the makeup of the mobile phase is subject to change over time, then at a common linear distance from the mobile phase inlet it is desirable for mobile phase to have a substantially identical composition from one column to the next. This is achieved with the device 200 due to two factors: (1) volume of the path of each (split) mobile phase solvent substream is substantially the same to each column; and (2) each flow path downstream of the fluidic (mobile phase and sample) inlets is characterized by substantially the same impedance.

The first factor, substantially equal substream flow paths, is promoted by design of the mobile phase distribution network 250. The second factor, substantial equality of the impedance of each column, is promoted by both design of the fluidic device 200 (including the slurry distribution network 264) and the simultaneous batch processing of multiple substantially identical columns 239A–239X via the common slurry network 264 from a common inlet port 261. During the packing process, with the multiple columns 239A–239X being in fluid communication from a common inlet 261, slurry flow within the device 200 is biased toward any low impedance region. The more slurry that flows to a particular column 239A–239X region during the packing process, the more particulate is deposited to locally elevate the impedance, thus yielding a self-correcting method for producing substantially equal impedance from one column to another.

While the embodiment illustrated in FIG. 4 and FIGS. 5A–5E represents a preferred fluidic device, one skilled in the art will recognize that devices according to a wide variety of other designs may be used, whether to perform parallel liquid chromatography or other fluid phase separation processes. For example, other functional structures, such as, but not limited to, sample preparation regions, fraction collectors, splitters, reaction chambers, catalysts, valves, mixers, and/or reservoirs may be provided to permit complex fluid handling and analytical procedures to be executed within a single device and/or system.

Preferred Fluidic Seals

Preferred fluidic interfaces according to the present invention include a microfluidic device having a narrowed near-surface channel, along with an external fluidic seal adapted to mate with the microfluidic device at an elevated contact pressure. The microfluidic device is preferably supported by a support surface or equivalent support structure. An actuator may be coupled to the fluidic seal or support surface to depress the fluidic seal (or at least a portion thereof, such as a protruding feature) against an outer surface of the microfluidic device. Or, as will be recognized by the skilled artisan, an equivalent result may be obtained by depressing at least a portion of the outer layer of the microfluidic device against a fluidic seal. In a preferred embodiment, the fluidic seal includes at least one protruding feature such as a boss. In one embodiment, the protruding feature comprises a continuous raised feature, such as an annulus, posited to mate with a fluidic port defined in an outer surface of a microfluidic device to promote even contact pressure distribution and eliminate easy pathways for fluid leakage.

Protruding features formed in fluidic seals may be provided in various shapes, including but not limited to annular, cylindrical, and cubic shapes. Individual protruding features may include fluidic passages intended to convey fluid to a desired location, or protruding features may lack passages to serve as plugs or stops to block fluid flow. In one embodiment, solid cylindrical protrusions (i.e., lacking fluidic passages defined within) may be substituted to provide sealing utility. This may be advantageous, for example, in providing an intermittent sealing utility along one or more sample loading ports of a microfluidic separation device, so as to permit the exposure of sample ports to receive samples when the fluidic seal is retracted, while preventing sample from leaking adjacent to the ports when the fluidic seal is depressed against the outer surface of such a separation device. A fluidic interface preferably prevents fluid leakage along a contact plane while either permitting or preventing fluid transmission through the protruding feature, depending on whether a fluidic passage is defined therein. In one embodiment, a fluidic interface includes multiple protruding features to permit simultaneous (parallel) interface with multiple fluidic ports defined in a microfluidic device. Various fluidic seals are disclosed in commonly assigned U.S. patent application Ser. No. 10/649,073 filed Aug. 26, 2003, which is hereby incorporated by reference.

In one embodiment, a fluidic seal is gasketless and includes non-elastomeric materials. A microfluidic device for use with such a seal may include a plastically deformable outer layer. Under the application of a compressive force, a protruding feature defined in the fluidic seal may plastically deform the outer layer of the microfluidic device to form a reverse impression or indentation of the protruding feature in the outer layer. The magnitude of the compressive force, the surface area of the protruding feature, and/or the geometry of the protruding feature may be adjusted to affect the contact pressure and thereby provide a desired level of sealing.

Preferably, materials used as contact surfaces of a fluidic seal are compatible with (i.e., non-absorptive of and non-degrading when placed into contact with chemicals typically used for performing liquid chromatography, including water, methanol, ethanol, isopropanol, acetonitrile, ethyl acetate, and dimethyl sulfoxide. The material(s) with which a fluidic seal are fabricated may be harder than the material of the outer layer of a corresponding microfluidic device intended to mate with the fluidic seal for wear resistance and to ensure that any plastic deformation caused by the interface occurs in the outer layer of the microfluidic device. For example, if a microfluidic device for use with a fluidic seal includes an outer layer fabricated with polypropylene, then preferred materials for fabricating the seal plate include, but are not limited to, poly (ether-ether-ketone) ("PEEK"), stainless steel, and anodized aluminum.

In further embodiments, gaskets and/or O-rings may be used along a sealing interface between a fluidic seal and a microfluidic device. Elastomeric materials including silicone may be used if desired.

Preferably, a compression element or clamping apparatus is provided to move any of the fluidic seal and at least the outer surface of a microfluidic device to promote sealing engagement along the interface. Preferably, the compression element or clamping apparatus includes at least one actuator to perform this task. Examples of clamping apparatuses are disclosed in commonly assigned U.S. patent application Ser. No. 10/649,073 and U.S. Patent Application Publication No. 20040089057, both of which are hereby incorporated by reference. Vertical translation of a platen portion of the apparatus may be facilitated by a piston-cylinder apparatus such as a pneumatic cylinder 210 (e.g., Bimba Flat-1 model FO-701.5-4R, Bimba Manufacturing Co., Monee, Ill.) operated by a feed of compressed gas from an external gas source such as a tank of compressed nitrogen. In one embodiment, compressed nitrogen regulated to about 140 psi (965 kPa) with an external pressure regulator is supplied to a pneumatic cylinder. As will be recognized by one skilled in the art, various types of actuators could be substituted for the pneumatic cylinder 210, including a hydraulic piston, a rotary screw, a solenoid, and/or a linear actuator.

Analytical Systems

While the fluidic interfaces described herein may be used with systems directed to a variety of different applications, one preferred application includes high performance liquid chromatography. A system for performing high-throughput pressure-driven liquid chromatography is shown in FIG. 6.

The system 300 preferably includes at least one (preferably at least two) solvent reservoir(s) 302 and pump(s) 304 for each solvent. Reservoirs 302 and pumps 304 for two or more solvents may be provided to permit operation of the system 300 in gradient mode, in which the mobile phase solvent composition is varied with respect to time during a particular separation run. Preferred pumps include conventional high-pressure liquid chromatography (HPLC) pumps such as Alcott Model 765 HPLC pumps with microbore heads (Alcott Chromatography, Norcross, Ga.). A pulse damper 306 is preferably provided downstream of the pump(s) 304 to reduce pulsations or variations in the mobile phase solvent supply pressure. A conventional micromixer (not shown) may be disposed between the pulse damper 306 and a multi-column microfluidic separation device 300 (similar to the device 200 illustrated and described in connection with FIGS. 4 and 5A–5E). A sample source 315 is also provided to provide samples to the microfluidic device 301 (preferably in parallel to permit parallel chromatographic separations of different samples). For example, the sample source 315 may include multiple pipettors. The interface with the microfluidic device 301 is provided by way of a first seal 308A and a second seal 308B and one or more compression elements 310A, 310B that preferably include actuators (not shown). If desired, the seal plate 308A and sample inlet seal 308B may be moved individually by the compression elements 310A, 310B. The first seal 308A and the second seal 308B may be used to provide intermittent sample access to the device 301, to conduct mobile phase solvent to the device 301, and to convey eluate from the device 301 following chromatographic separation. Each seal 308A, 308B may be disposed on the same side of the device 301 as illustrated, or the seals 308A, 308B may be disposed on opposite sides of the device 301. Support elements such as a support frame and/or support plate (not shown) may be disposed adjacent to the microfluidic device 301 to support the device 301 as it is compressed by any of the seals 308A, 308B. Further details regarding compression elements and seals for interfacing with microfluidic devices are disclosed in commonly assigned U.S. Patent Application Publication No. 2004/0089607 entitled "System and method for performing multiple parallel chromatographic separations," which is hereby incorporated by reference.

Downstream of the separation device 301, and detector 318 preferably having multiple detection regions (not shown), one detection region corresponding to each separation column of the microfluidic device 301. While various detection technologies may be used, the detector 318 preferably includes an electromagnetic source and an electromagnetic receiver such as may be used for UV-Visible detection or fluorescence detection. It will be readily apparent to one skilled in the art that the detector 318 may be adapted to perform the desired detection on the eluate stream while it is still in the device 301 or in a flow cell (not shown) downstream of the device 301. Downstream of the detector 318, eluate may be collected (e.g., for further analysis by mass spectrometric or similar consumptive techniques) or discarded in a collection or waste region 320.

Although embodiments of the present invention has been described in detail by way of illustration and example to promote clarity and understanding, it will be apparent that certain changes and modifications may be practiced within the scope of the appended claims.

What is claimed is:

1. A fluidic system comprising:
    a microfluidic device having an outer surface defining a fluidic port, the device defining a fluid flow path and defining a first microfluidic channel having a first width and being disposed within the device at a first depth relative to the outer surface;

a fluidic seal adapted to seal against the outer surface adjacent to the fluidic port; and a compression element adapted to move any of the fluidic seal and the outer surface;

wherein the first width is less than about two times the first depth; and wherein the fluidic seal engages the first cover layer and exerts a contact pressure of at least about 10 pounds per square inch against at least a portion of the outer surface without substantially occluding the fluid flow path.

2. The system of claim 1 wherein the width is less than about the first depth.

3. The system of claim 1, further comprising a source of pressurized fluid in fluid communication with the microfluidic device by way of the fluidic seal, the system being adapted to remain substantially sealed at a fluidic supply pressure of at least about 100 pounds per square inch.

4. The system of claim 1, further comprising a source of pressurized fluid in fluid communication with the microfluidic device by way of the fluidic seal, the system being adapted to remain substantially sealed at a fluidic supply pressure of at least about 250 pounds per square inch.

5. The system of claim 1 wherein the microfluidic device comprises a first stencil layer disposed between a first cover layer and a second cover layer, and the first microfluidic channel is defined through the entire thickness of the first stencil layer.

6. The system of claim 1 wherein:
the microfluidic device comprises a plurality of substantially planar device layers;
the first channel is defined in a second device layer of the plurality of device layers;
the fluidic port is defined in a first device layer of the plurality of device layers and comprises an elongated shape disposed lengthwise substantially perpendicular to the first channel; and
the second device layer is adjacent to the first device layer, with the first channel being in fluid communication with the fluidic port.

7. The system of claim 1 wherein the fluidic seal comprises a gasket.

8. The system of claim 1 wherein the fluidic seal comprises a plurality of bosses.

9. The system of claim 8 wherein each boss of the plurality of bosses is annular in shape.

10. The system of claim 1 wherein the fluidic seal comprises a plurality of O-rings.

11. The system of claim 1 wherein the fluidic seal comprises a plurality of fluidic passages or conduits.

12. The system of claim 1 wherein the microfluidic device comprises a plurality of microfluidic separation columns, each column of the plurality of columns containing stationary phase material and being adapted to perform pressure-driven liquid chromatography.

13. The system of claim 12 wherein the microfluidic device is adapted to operate at an internal fluid pressure of at least about 100 pounds per square inch.

14. The system of claim 1 wherein the fluidic seal has a sealing surface, the sealing surface comprises a non-elastomeric material, and the first cover layer comprises a non-elastomeric material.

15. The system of claim 1 wherein the outer surface comprises a polymeric material.

16. The system of claim 1 wherein the first depth is less than about 0.010 inch.

17. A fluidic system comprising:
a microfluidic device defining a fluid flow path, the device comprising a plurality of device layers including a first cover layer, a second cover layer, and a plurality of channel-defining stencil layers disposed between the first cover layer and the second cover layer, the first cover layer defining a plurality of fluid ports and the plurality of stencil layers including a first stencil layer disposed adjacent to the first cover layer;
a fluidic seal adapted to seal against the first cover layer;
a compression element adapted to move any of the fluidic seal and the first cover layer;
wherein the first cover layer has a first thickness, the first stencil layer defines a first microfluidic channel having a first width and in fluid communication with a first port of the plurality of fluid ports, the first width being less than about two times the first thickness; and
wherein the fluidic seal engages the first cover layer and exerts a contact pressure of at least about 10 pounds per square inch against at least a portion of the first cover layer without substantially occluding the fluid flow path.

18. The system of claim 17 wherein the first width is less than about the first thickness.

19. The system of claim 17, further comprising a source of pressurized fluid in fluid communication with the microfluidic device by way of the fluidic seal, the system being adapted to remain substantially sealed at a fluidic supply pressure of at least about 100 pounds per square inch.

20. The system of claim 17, further comprising a source of pressurized fluid in fluid communication with the microfluidic device by way of the fluidic seal, the system being adapted to remain substantially sealed at a fluidic supply pressure of at least about 250 pounds per square inch.

21. The system of claim 17 wherein the plurality of stencil layers includes a second stencil layer defining a second microfluidic channel, the second microfluidic channel having a second width that is more than about two times the first width.

22. The system of claim 17 wherein the first port comprises an elongated shape disposed lengthwise substantially perpendicular to the first microfluidic channel.

23. The system of claim 17 wherein the fluidic seal comprises a gasket.

24. The system of claim 17 wherein the fluidic seal comprises a plurality of bosses.

25. The system of claim 24 wherein each boss of the plurality of bosses is annular in shape.

26. The system of claim 17 wherein the fluidic seal comprises a plurality of O-rings.

27. The system of claim 17 wherein the fluidic seal comprises a plurality of fluidic passages or conduits.

28. The system of claim 17 wherein the microfluidic device comprises a plurality of microfluidic separation columns, each column of the plurality of columns containing stationary phase material and being adapted to perform pressure-driven liquid chromatography.

29. The system of claim 28 wherein the microfluidic device is adapted to operate at an internal fluid pressure of at least about 100 pounds per square inch.

30. The system of claim 17 wherein the fluidic seal has a sealing surface, the sealing surface comprises a non-elastomeric material, and the first cover layer comprises a non-elastomeric material.

31. The system of claim 17 wherein the first cover layer comprises a polymeric material.

32. The system of claim 17 wherein the first cover layer has a thickness of less than about 0.010 inch.

33. A fluidic processing method comprising the steps of:
providing a microfluidic device having an outer surface defining a fluidic port, the device defining a fluid flow path and defining a first microfluidic channel having a first width and being disposed within the device at a first depth relative to the outer surface, wherein the first width is less than about two times the first depth;
providing a fluidic seal adapted to seal against the outer surface adjacent to the fluidic port; and
establishing a contact pressure between at least a portion of the fluidic seal and at least a portion of the outer surface of at least about 10 pounds per square inch without substantially occluding the fluid flow path.

34. The method of claim 33 wherein the fluidic seal defines a fluidic passage, the method further comprising the step of transferring fluid between the fluidic seal and the microfluidic device through the fluidic passage.

35. The method of claim 33, further comprising the step of supplying a first fluid to the microfluidic device at a fluidic supply pressure of at least about 100 pounds per square inch.

36. The method of claim 33, further comprising the step of operating the microfluidic device to perform at least one liquid chromatographic separation.

* * * * *

UNITED STATES PATENT AND TRADEMARK OFFICE
CERTIFICATE OF CORRECTION

PATENT NO. : 7,028,536 B2  Page 1 of 1
APPLICATION NO. : 10/880656
DATED : April 18, 2006
INVENTOR(S) : Christoph D. Karp et al.

It is certified that error appears in the above-identified patent and that said Letters Patent is hereby corrected as shown below:

In title page (56) in the References Cited: Other Publications section, page 2, second column, "Poole, Colin F., "8.4.2 Column Technology," *The essence of chromatography*, 2003 Elsevier B.V., Amsterdam, The Netherlands, pp. 664-668" should be -- "Poole, Colin F., "8.4.2 Column Technology," *The essence of chromatography*, 2003 Elsevier Science B.V., Amsterdam, The Netherlands, pp. 664-668"--

In title page (56) in the References Cited: Other Publications section, page 2, second column, "Manz, Andreas et al., *Miniaturization fo Separation Techniques Using Planar Chips Technology*, "Journal of High Resolution Chromatography," vol. 16, Jul 1993" should be -- Manz, Andreas et al., *Miniaturization of Separation Techniques Using Planar Chips Technology*, "Journal of High Resolution Chromatography," vol. 16, Jul 1993 --

Column 2, line 36, "Internationial" should be -- International --

Signed and Sealed this

Twenty-first Day of November, 2006

JON W. DUDAS
*Director of the United States Patent and Trademark Office*